(12) United States Patent
Folan et al.

(10) Patent No.: US 11,666,429 B2
(45) Date of Patent: Jun. 6, 2023

(54) STENTS, SYSTEMS, AND METHODS FOR GASTROINTESTINAL TRACT TREATMENT

(71) Applicants: Boston Scientific Scimed, Inc., Maple Grove, MN (US); Universite Libre De Bruxelles, Brussels (BE); Brussels Medical Device Center, Brussels (BE)

(72) Inventors: Martyn G. Folan, Galway (IE); Jacques Deviere, Nivelles (BE); Nicolas Cauche, Brussels (BE); Thomas M. Keating, Galway (IE); Martin Burke, Galway (IE); Daniel Tuck, Galway (IE); Cecilia Delattre, Brussels (BE)

(73) Assignees: BOSTON SCIENTIFIC SCIMED, INC., Maple Grove, MN (US); UNIVERSITE LIBRE DE BRUXELLES, Brussels (BE); BRUSSELS MEDICAL DEVICE CENTER, Brussels (BE)

( * ) Notice: Subject to any disclaimer, the term of this patent is extended or adjusted under 35 U.S.C. 154(b) by 172 days.

(21) Appl. No.: 16/930,411

(22) Filed: Jul. 16, 2020

(65) Prior Publication Data
US 2021/0015598 A1 Jan. 21, 2021

Related U.S. Application Data

(60) Provisional application No. 62/875,267, filed on Jul. 17, 2019.

(51) Int. Cl.
*A61F 2/04* (2013.01)
*A61F 2/00* (2006.01)
*A61F 2/91* (2013.01)

(52) U.S. Cl.
CPC .............. *A61F 2/04* (2013.01); *A61F 2/0077* (2013.01); *A61F 2/91* (2013.01);
(Continued)

(58) Field of Classification Search
CPC .. A61F 2/04; A61F 2/0077; A61F 2/91; A61F 2002/044; A61F 2002/045;
(Continued)

(56) References Cited

U.S. PATENT DOCUMENTS 5,667,523 A 9/1997 Bynon et al.
5,876,445 A 3/1999 Andersen et al.
(Continued)

FOREIGN PATENT DOCUMENTS

CN 103876868 A 6/2014
JP 2005500890 A 1/2005
(Continued)

OTHER PUBLICATIONS

Murino, A., et al. (2015)—"Effectiveness of Endoscopic Management Using Self-Expandable Metal Stents in a Large Cohort of Patients with Post-bariatric Leaks"—OBES SURG 25:1569-1576.
(Continued)

*Primary Examiner* — William H Matthews
(74) *Attorney, Agent, or Firm* — Seager, Tufte & Wickhem, LLP

(57) ABSTRACT

The present disclosure relates generally to stents, systems, and methods for gastrointestinal treatment. In some embodiments, a stent may include a tubular scaffold having a first end opposite a second end, wherein a lumen extends between the first and second ends. The tubular scaffold may include a flared section and a medial section extending from the flared section, wherein a first diameter of the flared section is greater than a second diameter of the medial section. The stent may further include a liner extending
(Continued)

partially along a surface of the tubular scaffold, wherein the liner is spaced from an anchoring region of the flared section to promote tissue ingrowth with the flared section.

20 Claims, 13 Drawing Sheets

(52) U.S. Cl.
CPC ... *A61F 2002/044* (2013.01); *A61F 2002/045* (2013.01); *A61F 2210/0004* (2013.01); *A61F 2210/0014* (2013.01); *A61F 2220/0008* (2013.01); *A61F 2230/0026* (2013.01); *A61F 2230/0069* (2013.01); *A61F 2230/0071* (2013.01); *A61F 2250/0039* (2013.01); *A61F 2250/0048* (2013.01)

(58) Field of Classification Search
CPC ...... A61F 2210/0004; A61F 2210/0014; A61F 2220/0008; A61F 2230/0026; A61F 2230/0069; A61F 2250/0039; A61F 2250/0048; A61F 2/848; A61F 2002/009; A61F 2002/072; A61F 2002/828; A61F 2230/001; A61F 2230/0065; A61F 2250/0051; A61F 2/07
See application file for complete search history.

(56) References Cited

U.S. PATENT DOCUMENTS

| | | |
|---|---|---|
| 6,197,529 B1 | 3/2001 | Houghten et al. |
| 6,264,689 B1 | 7/2001 | Colgan et al. |
| 6,283,992 B1 | 9/2001 | Hankh et al. |
| 6,585,758 B1 | 7/2003 | Chouinard et al. |
| 7,311,031 B2 | 12/2007 | McCullagh et al. |
| 9,205,177 B2 | 12/2015 | Schorgl et al. |
| 9,517,122 B2 | 12/2016 | Firstenberg et al. |
| 9,801,749 B2 | 10/2017 | Hingston et al. |
| 10,052,220 B2 | 8/2018 | Ryan et al. |
| 10,130,502 B2 | 11/2018 | Chamorro et al. |
| 10,307,280 B2 | 6/2019 | Zeiner et al. |
| 10,420,665 B2 | 9/2019 | Sharma et al. |
| 10,548,753 B2 | 2/2020 | Rousseau |
| 10,682,220 B2 | 6/2020 | Folan et al. |
| 10,779,967 B2 | 9/2020 | Walsh et al. |
| 2003/0149472 A1 | 8/2003 | Pinchuk et al. |
| 2005/0085923 A1 | 4/2005 | Levine et al. |
| 2009/0210048 A1 | 8/2009 | Amplatz et al. |
| 2010/0106235 A1 | 4/2010 | Kariniemi et al. |
| 2010/0228335 A1 | 9/2010 | Schorgl et al. |
| 2011/0087146 A1 | 4/2011 | Ryan et al. |
| 2011/0106273 A1 | 5/2011 | Belhe et al. |
| 2011/0270391 A1 | 11/2011 | Chiltre et al. |
| 2011/0307070 A1* | 12/2011 | Clerc .................... B29C 41/06 623/23.7 |
| 2011/0319980 A1 | 12/2011 | Ryan |
| 2012/0065571 A1 | 3/2012 | Thompson et al. |
| 2012/0184893 A1 | 7/2012 | Thompson et al. |
| 2014/0121759 A1 | 5/2014 | Cully |
| 2014/0194805 A1 | 7/2014 | Levine et al. |
| 2014/0222039 A1 | 8/2014 | Khrosrovaninejad |
| 2014/0243950 A1 | 8/2014 | Weiner |
| 2014/0277443 A1 | 9/2014 | Fleury et al. |
| 2014/0343683 A1 | 11/2014 | Jeon et al. |
| 2014/0350694 A1 | 11/2014 | Behan |
| 2015/0045908 A1 | 2/2015 | McMahon |
| 2015/0131515 A1 | 5/2015 | Lavi et al. |
| 2015/0282922 A1 | 10/2015 | Hingston et al. |
| 2015/0374484 A1 | 12/2015 | Hingston et al. |
| 2016/0058914 A1 | 3/2016 | Bangera et al. |
| 2016/0095724 A1 | 4/2016 | Harris et al. |
| 2016/0296317 A1 | 10/2016 | Timmermans et al. |
| 2017/0100332 A1 | 4/2017 | Tonkin et al. |
| 2017/0216543 A1 | 8/2017 | Magin et al. |
| 2017/0325983 A1* | 11/2017 | Valdes ...................... A61F 2/90 |
| 2018/0036109 A1 | 2/2018 | Karavany et al. |
| 2018/0125630 A1* | 5/2018 | Hynes ...................... A61F 2/90 |
| 2018/0250118 A1 | 9/2018 | Folan et al. |
| 2018/0360589 A1* | 12/2018 | Nolan ...................... A61F 2/91 |

FOREIGN PATENT DOCUMENTS

| | | |
|---|---|---|
| JP | 2007513743 A | 5/2008 |
| JP | 2012506726 A | 3/2012 |
| JP | 2012519543 A | 8/2012 |
| JP | 2014521390 A | 8/2014 |
| KR | 1020130004575 U | 7/2013 |
| WO | 03020173 A1 | 3/2003 |
| WO | 2004049982 A2 | 6/2004 |
| WO | 2005058201 A1 | 6/2005 |
| WO | 2010051121 A1 | 5/2010 |
| WO | 2010101780 A2 | 9/2010 |
| WO | 2012128032 A1 | 9/2012 |
| WO | 2015195893 A1 | 12/2015 |

OTHER PUBLICATIONS

Eisendrath, P., et al. (2007)—"Endotherapy including temporary stenting of fistulas of the upper gastrointestinal tract after laparoscopic bariatric surgery"—Endoscopy. Jul. 2007;39(7):625-30.
Van Boeckel, P. et al. (2015)—"Refractory Esophageal Strictures: What To Do When Dilation Fails"—Curr Treat Options Gastroenterol. 2015; 13 (1):47-58.
Rebibo, L. et al. (2015)—"Combined stents for the treatment of large gastric fistulas or stenosis after sleeve gastrectomy"—Endoscopy 2015; 47: E59-E60.
Philip, G., (2018)—"EUS-guided gastrojejunostomy with lumen apposing metal stent versus enteral stent placement for palliation of malignant gastric outlet obstruction" Gastrointestinal Endoscopy vol. 87, No. 6S: 2018.
Betzel, B., (2017)—"Weight reduction and improvement in diabetes by the duodenaljejunal bypass liner: a 198 patient cohort study"—Surg Endosc (2017) 31:2881-2891.
International Search Report and Written Opinion for the International Patent Application No. PCT/US2020/042290, dated Oct. 2, 2020, 12 pages.
Hirdes et al., "Stent-in-Stent Technique for Removal of Embedded Esophageal Self-Expanding Metal Stents," Am J Gastroenterol 2011; 106:286-293.
Davee et al., "Stent-in-stent Technique for Removal of Embedded Partially Covered Self-Expanding Metal Stents", Surg Endosc, vol. 30, 2332-2341, 2016.
Deviere et al., Effectiveness of Endoscopic Management Using Self-Expandable Metal Stents in a Large Cohort of Patients with Post-bariatric Leaks, Obes Surg., vol. 25, 1569-1576, 2015.
WallFlex™ Esophageal Stents—Full and Partially Covered Self Expanding Metal Stents—Boston Scientific product brochure © Oct. 2016.
Ultraflex™ Esophageal NG Stent System—Boston Scientific product brochure © May 2018.
Ultraflex™ Single-Use Tracheobronchial Stent System—Boston Scientific product brochure © Oct. 2014.
Goyal RK, Chaudhury A. Physiology of normal esophageal motility, J. Clin Gastroenterol, 2008; 42(5): 610-619.
Mittal RK, Motor Function of the Pharynx, Esophagus and its Sphincters San Rafael (CA): Morgan & Claypool Life Sciences; 2011. Lower Esophageal Sphincter.

* cited by examiner

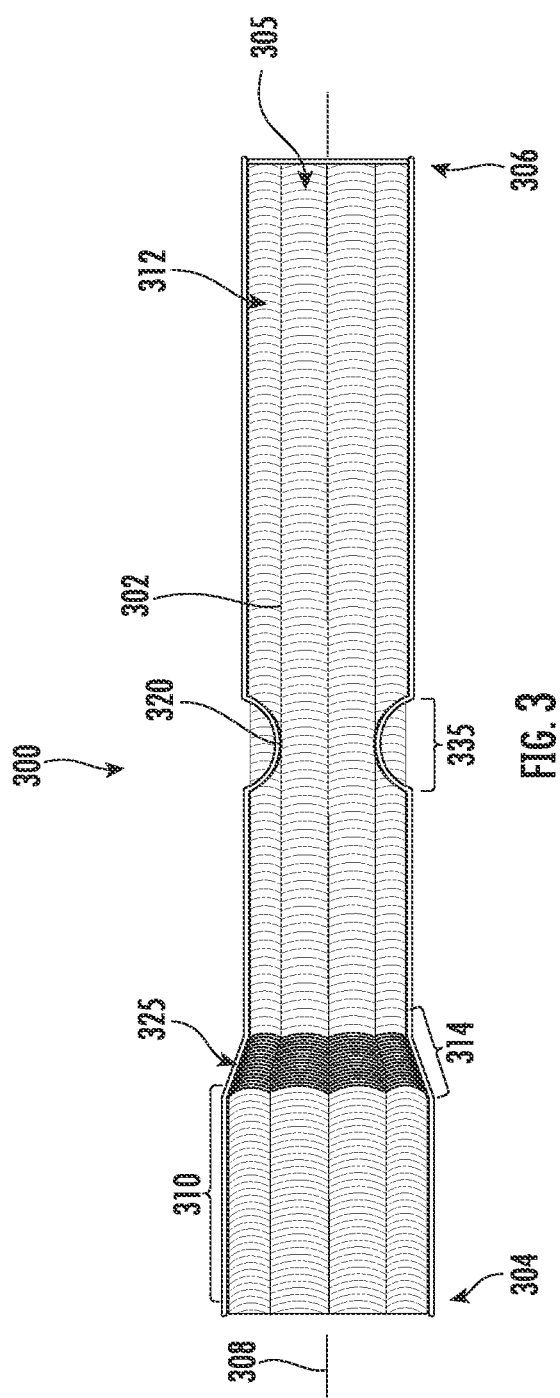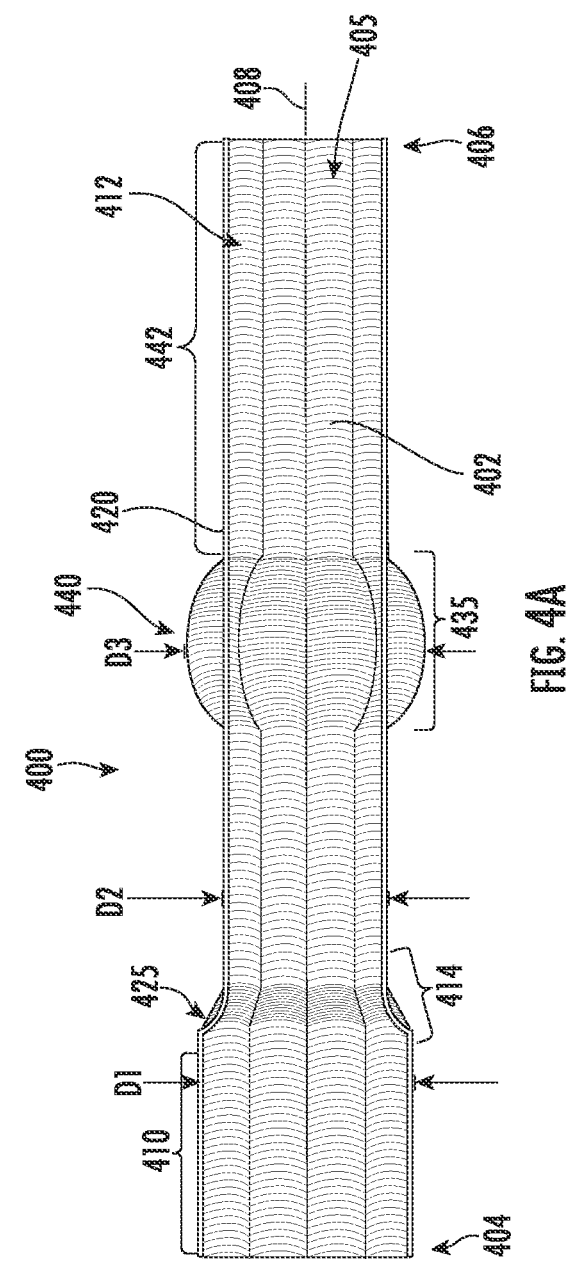

STENTS, SYSTEMS, AND METHODS FOR GASTROINTESTINAL TRACT TREATMENT

CROSS-REFERENCE TO RELATED APPLICATIONS

The present application claims the benefit of priority under 35 U.S.C. § 119 to U.S. Provisional Patent Application 62/875,267, filed Jul. 17, 2019, which application is incorporated herein by reference in its entirety for all purposes.

FIELD

The present disclosure relates to implantable medical devices and, more particularly, to stents, systems, and methods for gastrointestinal tract treatment.

BACKGROUND

Implantable medical devices, such as expandable stents, may be designed to provide a pathway for digested material, blood, or other fluid to flow therethrough following a medical procedure. Further, some implantable medical devices may incorporate features that aid in fistula treatment, bypass procedures, and/or anastomosis treatment. These implantable medical devices may include radially or self-expanding stents, which may be implanted transluminally via an endoscope. Additionally, some stents may be implanted in a variety of body lumens such as the esophageal tract, the gastrointestinal tract (e.g., the intestine, stomach, and the colon), tracheobronchial tract, urinary tract, biliary tract, vascular system, etc.

In some stents, the compressible and flexible properties that assist in stent positioning may also result in stent migration. For example, stents that are designed to be positioned in the esophageal or gastrointestinal tract may have a tendency to migrate due to peristalsis, which is an involuntary constriction and relaxation of the muscles of the esophagus, intestine, and colon. Additionally, the generally moist and inherently lubricious environment of the esophagus, intestine, colon, etc., further contributes to the tendency for stents to migrate after deployment. One approach to reduce stent migration includes exposing bare metal portions of the stent to tissue of the body lumen. The stent scaffold may provide a structure that promotes tissue ingrowth therewith to promote a hyperplastic response.

Additionally, some stents may be later removed from, or re-positioned within, the body lumen post-deployment. One approach to reduce the force necessary to remove stents includes providing a covering over a portion of the stent, thereby creating a physical barrier between the body lumen and the outer surface of the stent to reduce tissue ingrowth. However, covered stents may be more prone to migration than bare stents, as discussed above.

SUMMARY

The present disclosure in its various embodiments relates generally to stents, systems, and methods for gastrointestinal treatment. In one or more embodiments, a stent, may include a tubular scaffold having a first end opposite a second end, wherein a lumen extends between the first and second ends. The tubular scaffold may include a flared section, a medial section extending from the flared section, wherein a diameter of the flared section is greater than a diameter of the medial section, and a liner extending partially along a surface of the tubular scaffold, wherein the liner is spaced from an anchoring region of the flared section to promote tissue ingrowth with the flared section. In some embodiments, the liner is spaced apart from a medial anchoring region of the medial section to promote tissue ingrowth with the medial section. In some embodiments, the medial anchoring region is provided at an expanded portion of the medial section, and wherein the expanded portion has a third diameter greater than the diameter of the medial section. In some embodiments, the liner is spaced from the expanded portion to promote tissue ingrowth with the expanded portion. In some embodiments, the anchoring region is located along a sloped portion of the flared section, and wherein the sloped portion extends away from a central longitudinal axis extending through the lumen. In some embodiments, the medial section has a substantially uniform diameter. In some embodiments, the flared section has a first scaffold configuration, wherein the medial section has a second scaffold configuration, and wherein the first and second scaffold configurations are different.

In one or more embodiments, a system may include a stent comprising a tubular scaffold having a first end opposite a second end, wherein a lumen extends between the first and second ends. The tubular scaffold may include a flared section and a medial section extending from the flared section, wherein a first diameter of the flared section is greater than a second diameter of the medial section. The stent may further include a liner extending partially along a surface of the tubular scaffold, wherein the liner is spaced from an anchoring region of the flared section to promote tissue ingrowth with the flared section. The system may further include a sheath extending from the second end of the tubular scaffold, the sheath having a proximal end opposite a distal end, wherein a lumen extends between the proximal and distal ends. In some embodiments, the system may include a second stent coupled to the distal end of the sheath. In some embodiments, the second stent may include a second tubular scaffold and a second liner extending partially along a surface of the second tubular scaffold. In some embodiments, the second tubular scaffold may include a second flared section, and a second medial section extending from the second flared section, wherein a first diameter of the second flared section is greater than a second diameter of the second medial section, and wherein the second liner is spaced from a second anchoring region of the second flared section to promote tissue ingrowth with the second flared section. In some embodiments, the liner is spaced apart from a medial anchoring region of the medial section to promote tissue ingrowth with the medial section. In some embodiments, the anchoring region is located along a sloped portion of the flared section, and wherein the sloped portion extends away from a central longitudinal axis extending through the lumen. In some embodiments, the medial section includes an expanded portion, the expanded portion having a third diameter greater than the diameter of the medial section. In some embodiments, the liner is spaced from the expanded portion to promote tissue ingrowth with the expanded portion. In some embodiments, the sheath comprises a structural support element.

In one or more embodiments, a method may include deploying a system within a gastrointestinal (GI) tract of a patient, the system including a stent having a tubular scaffold having a first end opposite a second end, wherein a lumen extends between the first and second ends. The tubular scaffold may include a flared section and a medial section extending from the flared section, wherein a diameter of the flared section is greater than a diameter of the medial section; and. The stent may further include a liner extending partially along a surface of the tubular scaffold, wherein the liner is spaced from an anchoring region of the flared section, and wherein the anchoring region is exposed to the GI tract to promote tissue ingrowth between the anchoring region and the GI tract. The method may further include positioning the flared section along one side of a GI tract target site, and positioning the medial section directly adjacent the GI tract target site. In some embodiments, the method may further include determining a location of the GI tract target site, wherein the GI tract target site corresponds to a leak of the GI tract. In some embodiments, the method may further include bypassing a portion of the GI tract using a sheath extending from the second end of the tubular scaffold, the sheath having a proximal end opposite a distal end, wherein a lumen extends between the proximal and distal ends. In some embodiments, the method may include securing a second stent within the GI tract, the second stent coupled to the distal end of the sheath.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures:

FIG. 3 is a side view of a stent according to embodiments of the present disclosure;

FIGS. 4A-4E are side views of stents with various expanded portions according to embodiments of the present disclosure;

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As described above, self-expanding metal stents (SEMS) are used extensively in a minimally invasive manner throughout the gastrointestinal (GI) tract for the treatment of a myriad of disease states including, but not limited to, vessel lumen closure (e.g., stricture due to tumorous growth, surgical etiologies, etc.) and GI bypass complications (e.g., post bariatric leaks treatments). SEMS may be removable or permanent, dependent on the disease state under treatment, with removability typically defined by the presence or absence of a durable coating. Permanent SEMS may not have a coating, which when placed within the GI tract, allows for vessel tissue ingrowth due to stimulated hyperplasia of the vessel. Eventually the SEMS is embedded in place as a result of the tissue ingrowth.

As further described herein, embodiments of the present disclosure provide stents, systems, and methods for treatment of GI tract diseases for a consistent, repeatable approach for anti-migration to treat the myriad of underlying conditions. In some embodiments, a stent may include a tubular scaffold having a first end opposite a second end, wherein a lumen extends between the first and second ends. The tubular scaffold may include a flared section and a medial section extending from the flared section, wherein a diameter of the flared section is greater than a diameter of the medial section. The stent may further include a liner extending partially along a surface of the tubular scaffold, wherein the liner is spaced from an anchoring region of the flared section to promote tissue ingrowth with the flared section.

Figure 1A:
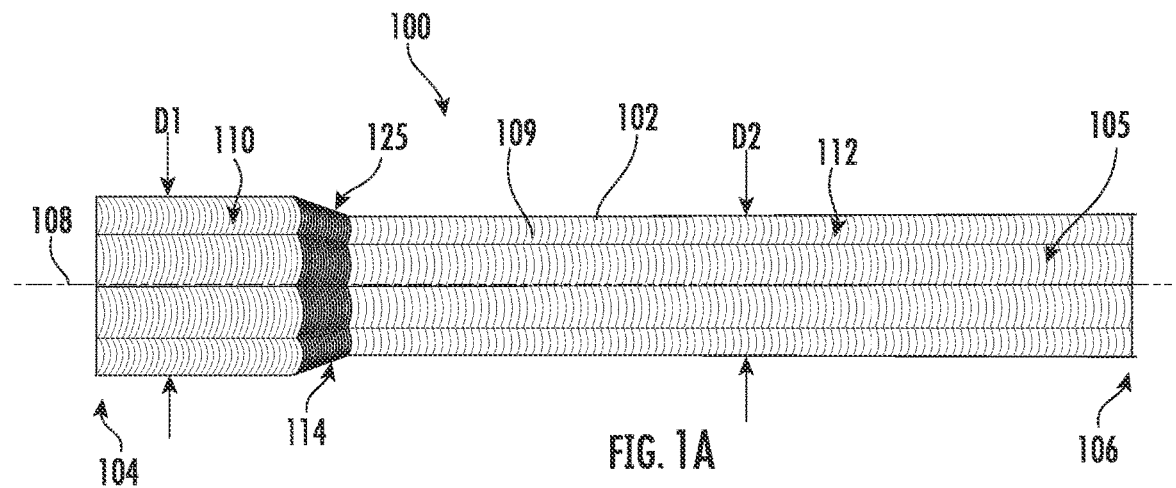
FIGS. 1A-1C are side views of stents according to embodiments of the present disclosure.

Turning now to FIG. 1A, a stent 100 according to embodiments of the disclosure will be described in greater detail. As shown, the stent 100 may include a tubular scaffold (hereinafter "scaffold") 102 having a first end 104 opposite a second end 106. The scaffold 102 may define a lumen 105 extending between the first end 104 and second end 106, for example, along a central longitudinal axis 108. When positioned in a body lumen, such as a patient's GI tract, the first end 104 (in this case, the proximal end) may be positioned closest to a patient's mouth.

Additionally, the stent 100 may include one or more strut members 109 forming the tubular scaffold 102. The strut members 109 may extend helically, longitudinally, circumferentially, or otherwise along stent 100. While FIG. 1A shows the strut members 109 generally extending along an entire length of the stent 100, the strut members 109 may extend only along a portion of the stent 100 in other embodiments.

As further shown, the scaffold 102 may include a flanged or flared section 110 connected to, or integrally formed with, a medial section 112. In some embodiments, a first diameter 'D1' of the flared section 110 may be greater than a second diameter 'D2' of the medial section 112. As shown, the medial section 112 may have a generally uniform diameter along its length. The flared section 110 may include a sloped portion 114 extending away from the central longitudinal axis 108. In some embodiments, the sloped portion 114 is at an intersection between the flared section 110 and the medial section 112.

In some embodiments, the stent 100 may be balloon or self-expanding. Self-expanding stent examples may include stents having one or more strut members 109 combined to form a rigid and/or semi-rigid stent structure. For example, the strut members 109 may be one or more wires or filaments which are braided, wrapped, intertwined, interwoven, weaved, knitted, looped (e.g., bobbinet-style), or the like to form the scaffold 102. Alternatively, the stent 100 may be a monolithic structure formed from a cylindrical tubular member, such as a single, cylindrical tubular laser-cut Nitinol tubular member, in which the remaining portions of the tubular member form the strut members 109. Openings or interstices through a wall of the stent 100 may be defined between adjacent the strut members 109.

The stent 100 may be constructed from a variety of non-limiting materials. For example, when balloon or self-expandable, the stent 100 may be constructed from a metal (e.g., Nitinol, Elgiloy, stainless steel, cobalt-chrome, positive temperature co-efficient of resistivity, etc.). In other examples, the stent 100 may be constructed from a polymeric material (e.g., polyethylene terephthalate, poly(m-ethyl methacrylate)). In yet other examples, the stent 100 may be constructed from a combination of metallic and polymeric materials. In still yet other examples, the stent 100 may include a bioabsorbable and/or biodegradable material (e.g., a poly(lactic-co-glycolic acid) polymer).

Figure 1B:
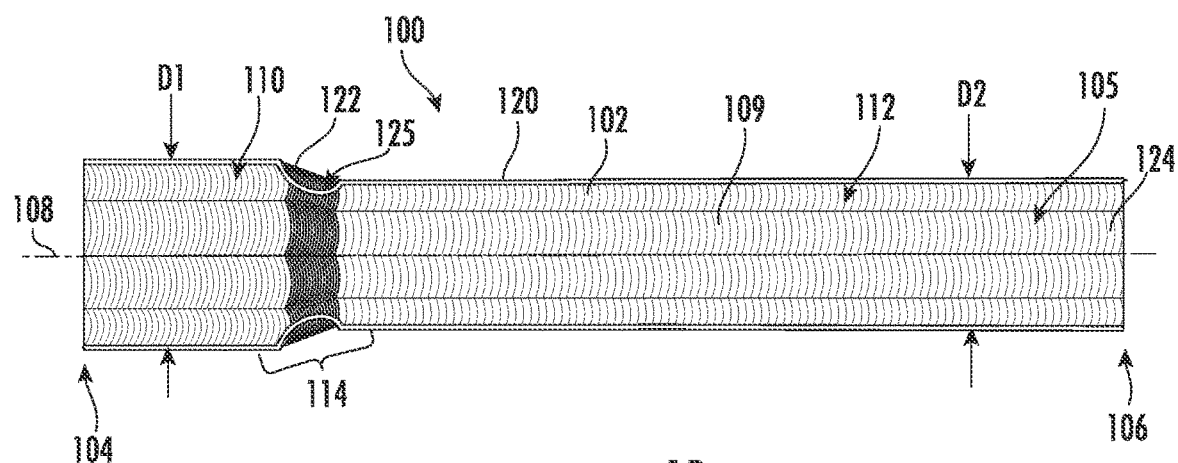

As shown in FIG. 1B, the stent 100 may include a liner 120 extending between the first end 104 and the second end 106. The liner 120 may be provided to maintain a passageway through the stent 100, as well as to prevent tissue ingrowth along the scaffold 102 in certain areas. In the non-limiting embodiment shown, the liner 120 may be formed over an exterior surface 122 of the scaffold 102. However, the liner 120 may be formed only partially along the exterior of the scaffold 102, as will be described in greater detail herein. In other embodiments, the liner 120 may be formed along an interior surface 124 of the scaffold 102. In yet other embodiments, the liner 120 may be formed along both the exterior surface and the interior surface 124 of the scaffold.

In various embodiments, the liner 120 may be a polymeric material, such as silicone, polyurethane, polyvinylidene difluoride (PVDF), Chronoflex®, or similar biocompatible polymeric formulations. In yet other embodiments, the liner 120 may include a ciliated coating (not shown) along an interior surface thereof. As shown, the liner 120 may extend between strut members 109, thereby filling any space between adjacent strut members 109 of the scaffold 102. Reference to a liner may be understood as a coating, where a portion of the coating is coupled to at least a portion of a stent, and a portion of the coating may be floating with respect to the stent.

In some embodiments, the liner 120 is spaced from an anchoring region 125 of the flared section 110 to promote tissue ingrowth between the GI tract and the anchoring region 125 of the flared section 110. For example, the liner 120 at the anchoring region 125 may extend radially inward towards the central longitudinal axis 108 such that the liner 120 is generally not in contact with the interior surface 124 of the scaffold 102. As a result, the anchoring region 125 may promote or allow tissue ingrowth to anchor the flared section 110 in place within the GI tract.

In some embodiments, the liner 120 may include an elastic material component configured to stretch radially inward, for example, as tissue grows through the interstices of the scaffold 102 in the anchoring region 125. The liner 120 may deflect, stretch, etc. radially inward in response to inward forces (e.g., tissue ingrowth) acting thereupon.

In other embodiments, it may be desirable to limit the amount of inward deflection of the liner 120. For example, the liner 120 may define a lumen extending therein, wherein the lumen is designed to permit food and/or or other digestible material to flow therethrough. Therefore, in some instances it may be desirable to design the liner 120 to preserve the passageway defined by the lumen 105. In other words, it may be desirable in some instances to prevent or minimize an amount the liner 120 closes radially. In some instances, the liner 120 may include reinforcing filaments (e.g., fibers) embedded in the material of the liner 120 that may be drawn taut after a threshold amount of stretching of the material of the liner 120 to prevent further stretching of the liner 120. In some instances, the reinforcement filaments may be arranged longitudinally, circumferentially, helically, randomly, or otherwise.

Examples of liners and stent/liner configurations may include, but are not limited to, those shown and described in U.S. Patent Application Publication No. US2018/0250118, filed Mar. 1, 2018, and titled "Esophageal Stent Including an Inner Liner," and U.S. Patent Application Publication No. US2018/0280167, filed Mar. 27, 2018, and titled "Retrievable Stent System," both of which applications are incorporated by reference herein in their entireties and for all purposes.

Figure 1C:
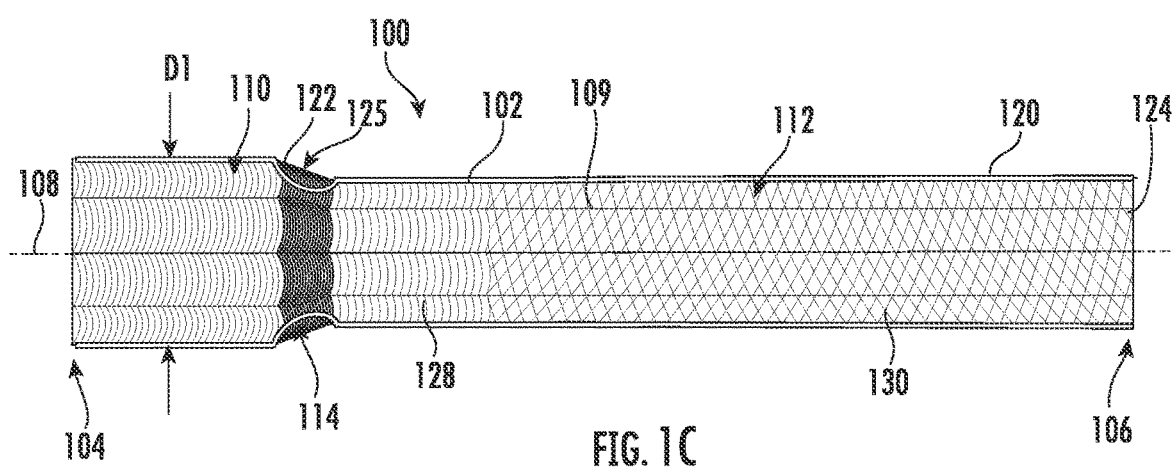

As demonstrated in FIG. 1C, the scaffold 102 may include multiple sections joined together. For example, the medial section 112 may include a first component 128 coupled to a second component 130. The first and second components 128, 130 may be joined together using any variety of attachment means. In the non-limiting embodiment shown, the strut members 109 of the first component 128 may be arranged in a first configuration, e.g., knitted, while the strut members 109 of the second component 130 may be arranged in a second configuration, e.g., braided. In some embodiments, the first component 128 and the second component 130 may have the same or different weave patterns. Embodiments herein are not limited in this context.

Figure 2:
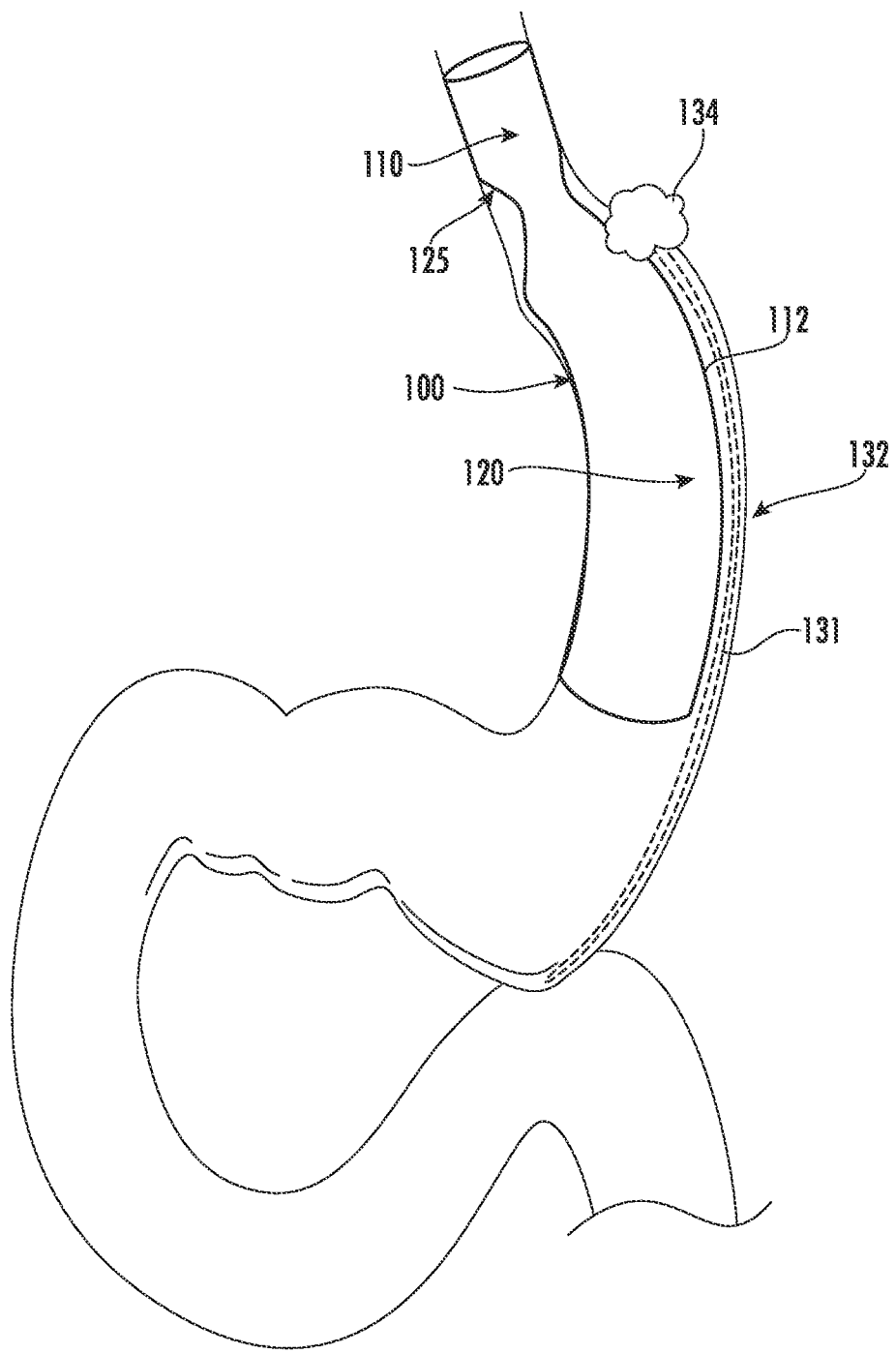
FIG. 2 depicts a stent within a GI tract of a patient according to embodiments of the present disclosure.

FIG. 2 illustrates the use of the stent 100 within a GI tract 132 of a patient according to embodiments of the present disclosure. In this non-limiting example, the GI tract 132 may include a staple line 131 as a result of a sleeve gastrectomy procedure, for example. As shown, the stent 100 may be deployed to a GI tract target site 134, which may correspond to a leak, perforation, or tear along the staple line 131. As shown, the flared section 110 may be positioned within a proximal section of the GI tract 132, in this instance the patient's esophagus, while the medial section 112 may extend down further into the GI tract 132, in this instance a stomach remnant. The anchoring region 125 of the flared section 110 may be provided adjacent the GI tract 132 to promote tissue ingrowth between the GI tract 132 and the flared section 110. Meanwhile, the liner 120 along the medial section 112 may be positioned directly adjacent the GI tract target site 134 to prevent or minimize the leak.

FIG. 3 demonstrates a stent 300 according to embodiments of the disclosure. The stent 300 may be the same or similar in many aspects to the stent 100 described above. As such, only certain aspects of the stent 300 may be described hereinafter for the sake of brevity.

As shown, the stent 300 may include a scaffold 302 having a first end 304 opposite a second end 306. The scaffold 302 may define a lumen 305 extending between the first end 304 and second end 306, for example, along a central longitudinal axis 308. The scaffold 302 may include a flared section 310 connected to, or integrally formed with, a medial section 312. The flared section 310 may include a sloped portion 314 extending away from the central longitudinal axis 308. In some embodiments, the sloped portion 314 joins the flared section 310 to the medial section 312.

As shown, the medial section 312 may include a medial anchoring region 335, which is a bare section of the scaffold 302 for promoting tissue ingrowth between the medial section 312 and a GI tract. As shown, a liner 320 extending along the scaffold 302 may be spaced from the medial anchoring region 335 to promote tissue ingrowth. In some embodiments, the liner 320 at the medial anchoring region 335 may extend radially inward towards the central longitudinal axis 308. The liner 320 may also be spaced from an anchoring region 325 of the flared section 310 to promote tissue ingrowth between the GI tract and the flared section 310. In some embodiments, the anchoring region 325 is located along the sloped portion 314. Once inserted within a patient, the anchoring region 325 of the flared section 310 may be positioned along one side of (e.g., above) a GI tract target site (not shown), while the medial anchoring region 335 of the medial section 312 may be positioned adjacent and/or below the GI tract target site to isolate a leak at the GI tract target site.

Figure 4B:
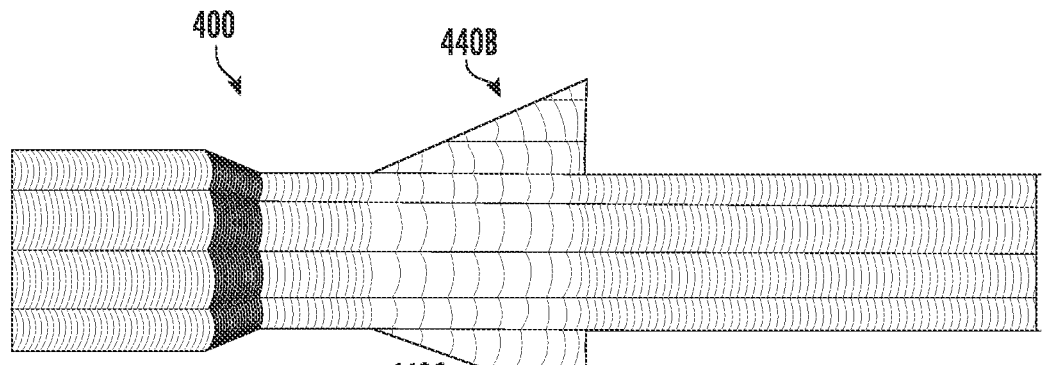

FIG. 4A demonstrates a stent 400 according to embodiments of the present disclosure. The stent 400 may be the same or similar in many aspects to the stents 100 and/or 200 described above. As such, only certain aspects of the stent 400 may be described hereinafter for the sake of brevity.

As shown, the stent 400 may include a scaffold 402 having a first end 404 opposite a second end 406. The scaffold 402 may define a lumen 405 extending between the first end 404 and second end 406, for example, along a central longitudinal axis 408. A liner 420 may be provided along the scaffold 402. The scaffold 402 may include a flared section 410 connected to, or integrally formed with, a medial section 412. In some embodiments, a first diameter 'D1' of the flared section 410 may be greater than a second diameter 'D2' of the medial section 412. The flared section 410 may include a sloped portion 414 extending away from the central longitudinal axis 408. In some embodiments, the sloped portion 414 joins the flared section 410 to the medial section 412.

As shown, the medial section 412 may include a medial anchoring region 435, which may be a bare spot/region along the scaffold 402 to promote tissue ingrowth between the medial section 412 and a GI tract. In some embodiments, the medial anchoring region 435 may be provided at an expanded portion 440 of the medial section 412. As shown, the expanded portion 440 may have a third diameter 'D3', which is greater than D2 of the medial section 412. The expanded portion 440 may have a curvature, e.g., expanding radially outward from the medial section 412, such that the third diameter D3 is the maximum diameter of the curvature. In some embodiments, D3 may also be greater than D1 of the flared section 410. In other embodiments, D3 is equal to or less than D1. Embodiments herein are not limited in this context.

As further shown, the liner 420 extending along the scaffold 402 may be spaced from the expanded portion 440 to promote tissue ingrowth along certain portions of the medial section 412, such as at the medial anchoring region 435. In some embodiments, the liner 420 located radially inward from the expanded portion 440 may curve or extend towards the central longitudinal axis 408. In other embodiments, the liner 420 may be generally straight at the expanded portion 440, as shown. Once inserted within a patient, an anchoring region 425 of the flared section 410 may be positioned along one side of (e.g., above) a GI tract target site (not shown), while the expanded portion 440 of the medial section 412 may be positioned at or below the GI tract target site. The anchoring region 425 may secure the flared section 410 within the GI tract, while the expanded portion 440 may interact with the GI tract target site to promote a hyperplastic response from the tissue of the GI tract. In some embodiments, a distal portion 442 of the medial section 412 may extend from the expanded portion 440, acting as a conduit to bypass the GI tract target site.

Figure 4C:
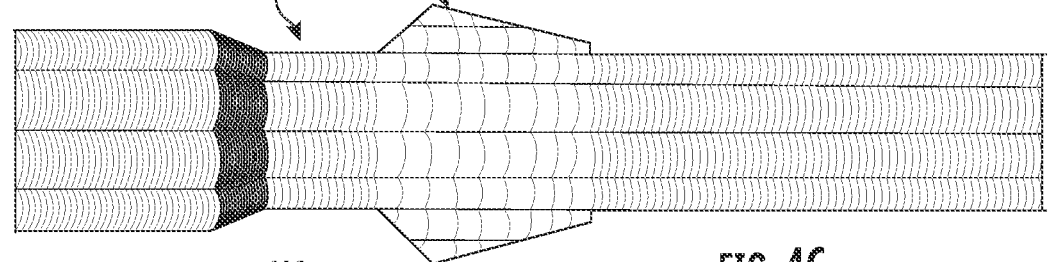
Figure 4D:
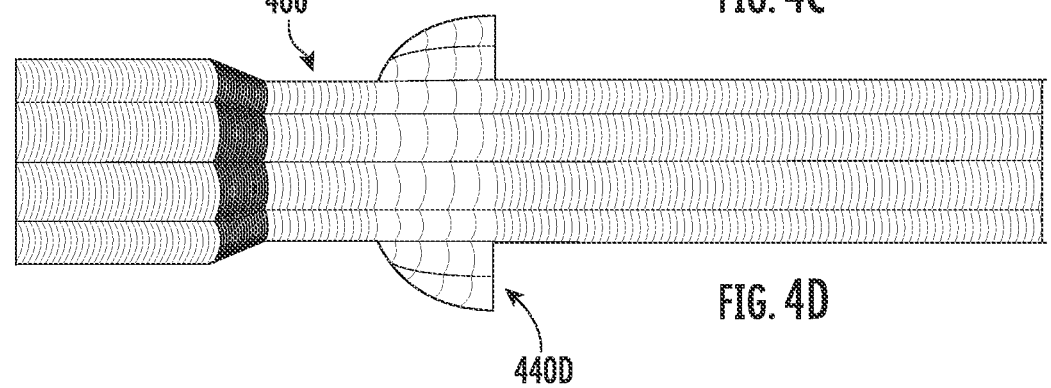

It will be appreciated that the expanded portion 440 may take on a variety of different configurations. For example, the expanded portion 440 of FIG. 4A may have a generally spherical shape cross-section, an expanded portion 440B of FIG. 4B may have a generally trapezoidal shape cross-section, an expanded portion 440C of FIG. 4C may have a generally pentagonal shape cross-section, and an expanded portion 440D of FIG. 4D may have a generally chordal shape cross-section. Embodiments herein are not limited in this context.

Figure 4E:
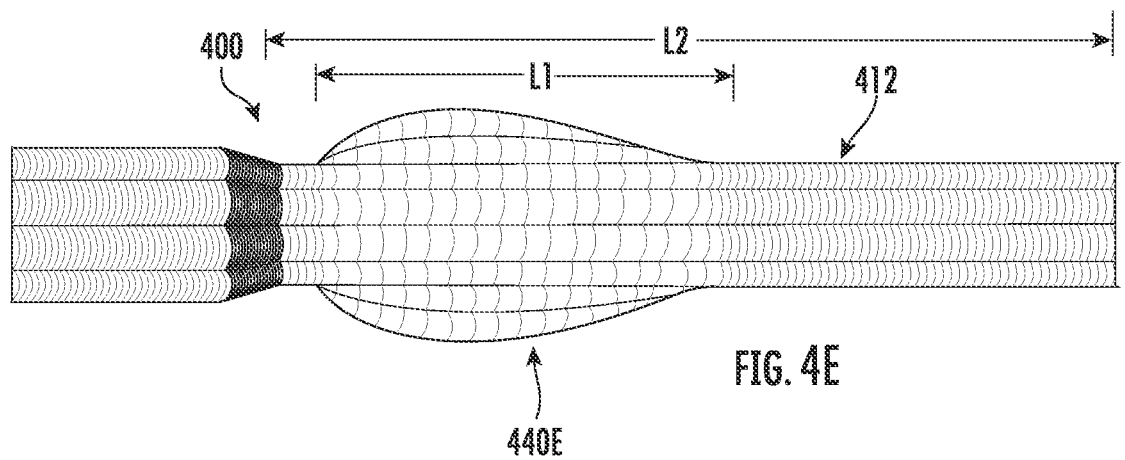

Furthermore, it will be appreciated that a length of the various expanded portion(s) 440A-440E may be modified to influence an amount of interaction between the medial anchoring region 435 and the GI tract. For example, as shown in FIG. 4E, a length 'L1' of the expanded portion 440E may be increased relative to an overall length 'L2' of the medial section 412. As will be appreciated, tissue ingrowth of the GI tract generally increases as the length L1 increases.

Figure 5A:
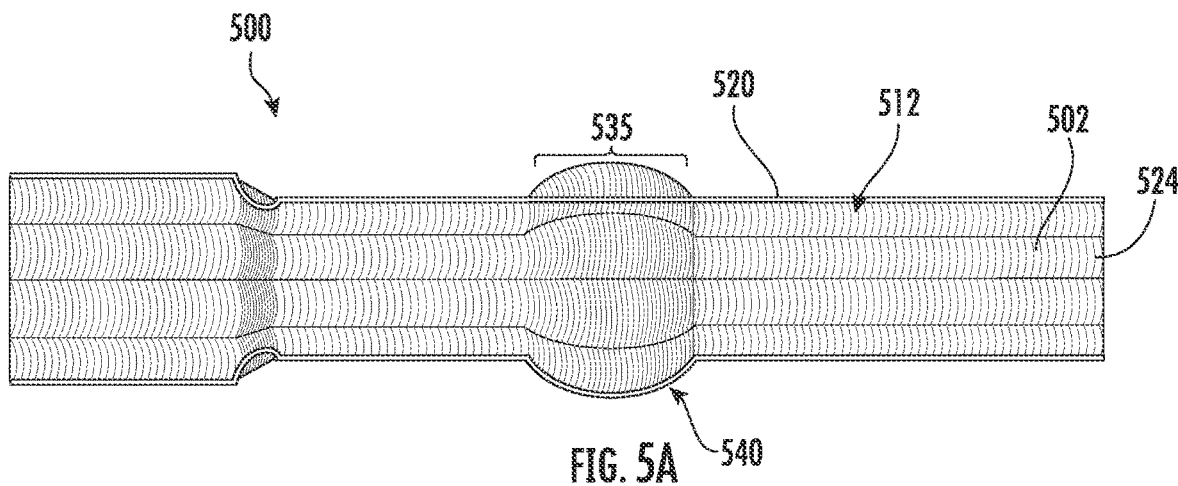
FIG. 5A is a side view of a stent including a liner having a recessed section according to embodiments of the present disclosure.
Figure 5B:
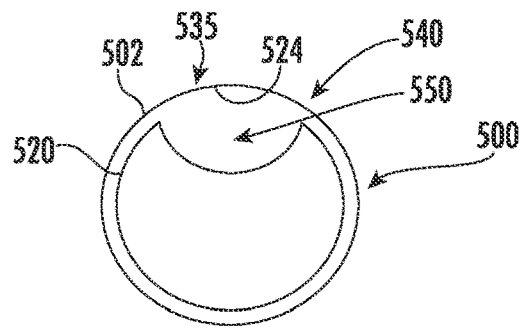
FIG. 5B is a cross-sectional view of the stent and a liner of FIG. 5A according to embodiments of the present disclosure.

Turning now to FIGS. 5A-5B, a liner 520 of a stent 500 according to embodiments of the present disclosure will be described in greater detail. As shown, the liner 520 may have a non-circular cross-section to promote tissue ingrowth between a scaffold 502 of the stent 500 and a GI tract. In this embodiment, the liner 520 may include a recessed section 550 spaced from an interior surface 524 of the scaffold 502. The recessed section 550 may provide a medial anchoring region 535 of the scaffold 502. In some embodiments, the medial anchoring region 535 may be provided at an expanded portion 540 of the medial section 512. In other embodiments, the medial section 512 may have a substantially constant diameter along its length.

Figure 6A:
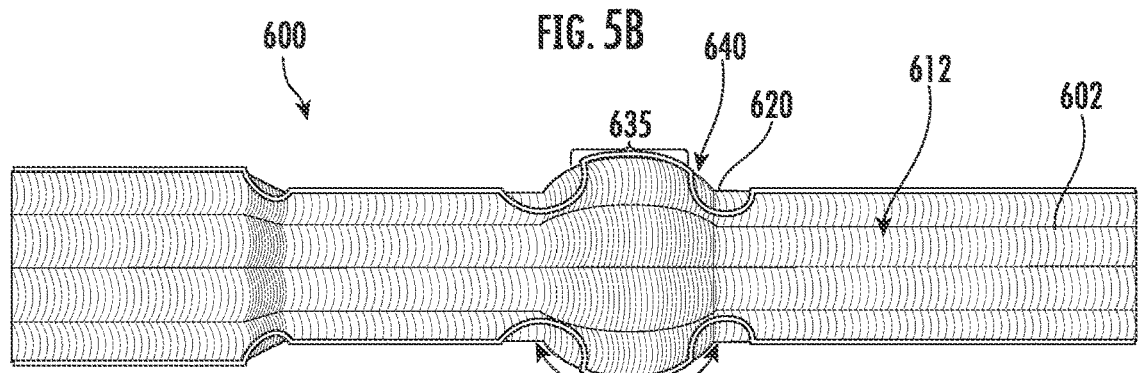
FIG. 6A is a side view of a stent including a liner having a recessed section according to embodiments of the present disclosure.
Figure 6B:
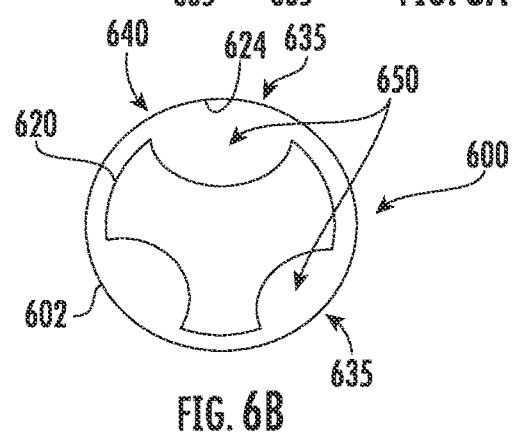
FIG. 6B is a cross-sectional view of a stent and liner similar to that of FIG. 6A and according to embodiments of the present disclosure.

In FIGS. 6A-6B, a liner 620 of a stent 600 may include a plurality of recessed sections 650 spaced from an interior surface 624 of a scaffold 602 of the stent 600. The recessed sections 650, which may be spaced apart circumferentially along the liner 620 (different configurations being shown in FIG. 6A and FIG. 6B as non-limiting examples), may provide a plurality of medial anchoring regions 635 along the scaffold 602 to promote tissue ingrowth between the scaffold 602 and the medial section 612. In some embodiments, the medial anchoring region 635 may be provided at an expanded portion 640 of the medial section 612. In other embodiments, the medial section 612 may have a substantially constant diameter along its length.

Figure 6C:
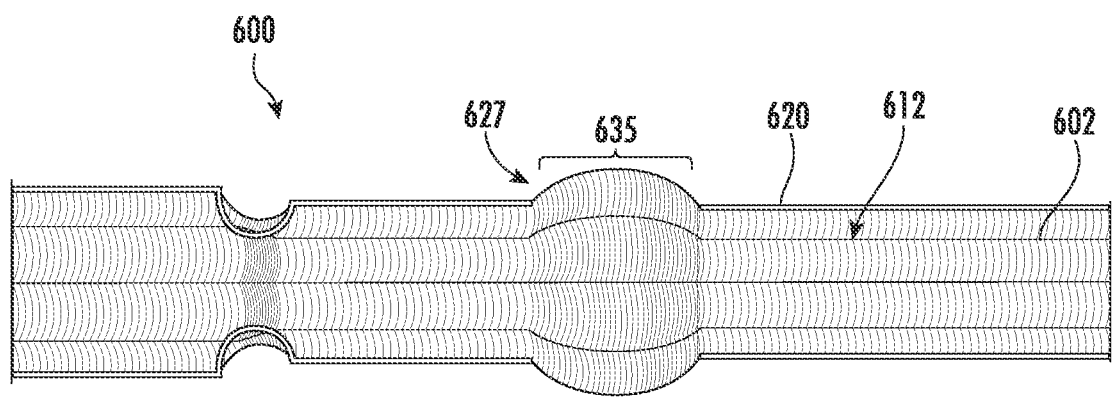
FIG. 6C is a side view of a stent including a liner having a recessed section according to embodiments of the present disclosure.

In yet other embodiments, as shown in FIG. 6C, the expanded portion 640 of the medial section 612 may not include the liner 620. Instead, the expanded portion 640 remains exposed to promote hyperplasia tissue growth 627 between a body lumen (not shown) and the exposed portion of the scaffold 602. The hyperplasia tissue growth 627 may act as a seal to form a continuous channel through an interior of the scaffold 602.

Figure 7:
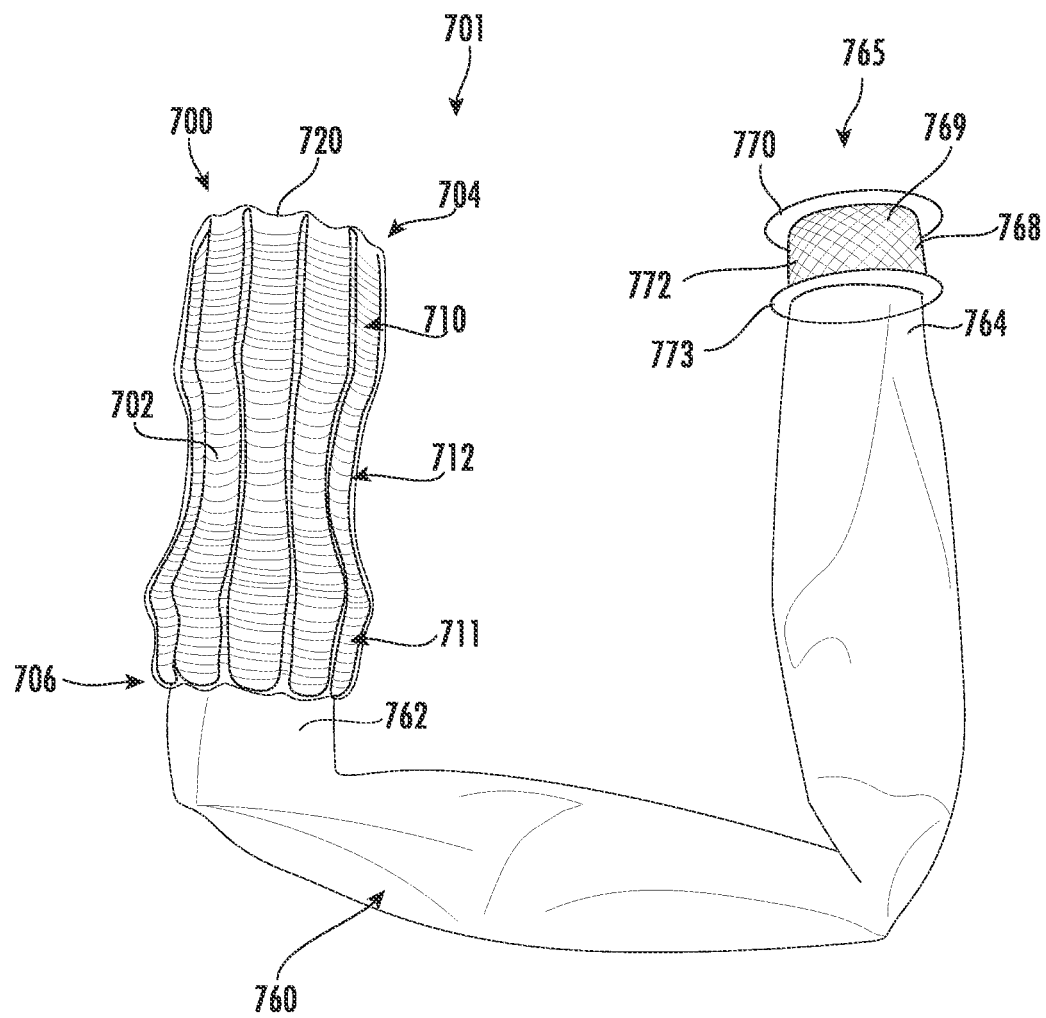
FIG. 7 is a perspective view of a system according to embodiments of the present disclosure.

Turning now to FIG. 7, a system 701 according to embodiments of the present disclosure will be described in greater detail. As shown, the system 701 may include a stent 700 having a tubular scaffold (hereinafter "scaffold") 702. The stent 700 may be the same or similar in many aspects to the stents 100, 300, 400, 500, and 600 described above. As such, only certain aspects of the stent 700 may be described hereinafter for the sake of brevity.

As shown, the stent 700 may include a first flared section 710 at a first end 704, and a second flared section 711 at a second end 706. Between the first flared section 710 and the second flared section 711 lies a medial section 712. As shown, the medial section 712 may have a reduced diameter as compared to the diameters of the first and second flared sections 710, 711. As further shown, the stent 700 may include a liner 720 disposed along a surface of the scaffold 702.

In some embodiments, a sheath 760 may be coupled to the second end 706 of the stent 700. The sheath 760 may be a flexible tube having a proximal end 762 and a distal end 764, the sheath 760 defining a lumen extending between the proximal and distal ends 762, 764. Although non-limiting, the sheath 760 may be Silicone, UE, PTFE, ePTFE, Chronoflex, PMMA, PVDF, and the like.

As further shown, the system 701 may include a second stent 765 coupled to the distal end 764 of the sheath 760. In some embodiments, the second stent 765 may include a second tubular scaffold (hereinafter "second scaffold") 768 defined by a plurality of stent members 769 arranged into any variety of configurations. The second scaffold 768 of the stent 765 may have a constant diameter or a varied diameter. For example, in the case of the latter, the second scaffold 768 may include a first flared section 770 connected to, or integrally formed with, a second medial section 772. In some embodiments, the second tubular scaffold 768 may include a second flared section 773 extending from an opposite side of the second medial section 772. In some embodiments, a diameter of the first and second flared sections 770, 773 of the second scaffold 768 is greater than a diameter of the second medial section 772. Embodiments herein are not limited in this context.

Although not shown, a second liner may extend along a surface (e.g., inner and/or outer) of the second scaffold 768. In some embodiments, the second liner may be spaced from the second scaffold 768 in one or more second anchoring regions to promote tissue ingrowth between the second scaffold 768 and a GI tract of a patient. In other embodiments, no liner is present along the second scaffold 768.

Figure 8A:
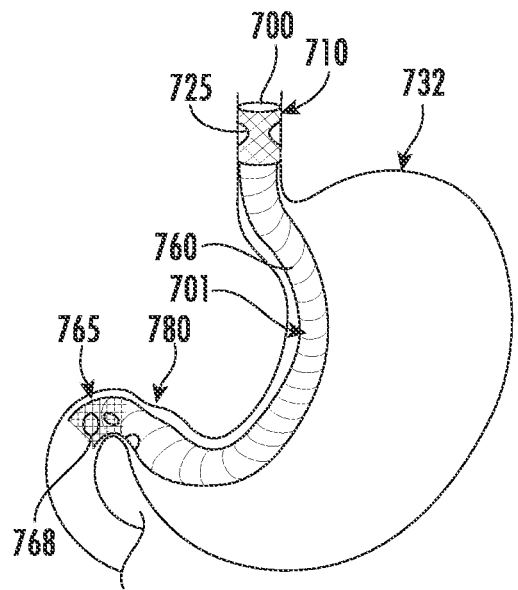
FIG. 8A demonstrates the system of FIG. 7 placed within a GI tract during a restrictive bariatric treatment according to embodiments of the present disclosure.
Figure 8B:
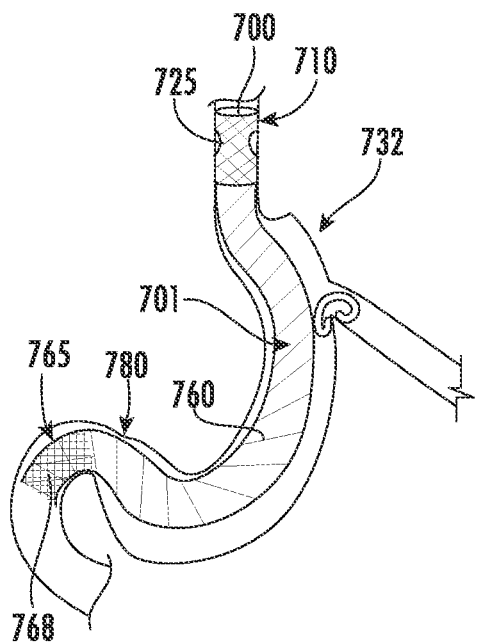
FIG. 8B demonstrates the system of FIG. 7 placed within a GI tract for treatment of leaks according to embodiments of the present disclosure.

FIGS. 8A-8B demonstrates an example use of the system 701 within a GI tract 732 of a patient according to embodiments of the present disclosure. Although non-limiting, FIG. 8A demonstrates the system 701 placed within the GI tract 732 for a restrictive bariatric treatment. As shown, the sheath 760 may bypass a portion of the GI tract 732. FIG. 8B demonstrates the system 701 used for treatment of gastrocutaneous fistulas. As shown, the stent 700 may be positioned within a proximal section of the GI tract 732, while the sheath 760 extends down further into the GI tract 732. An anchoring region 725 of the flared section 710 is provided directly adjacent an interior of the GI tract 732 to promote tissue ingrowth between the GI tract 732 and the flared section 710.

The second stent 765, which is coupled to the sheath 760, may also be positioned within the GI tract 732, for example, below a pyloric region 780 thereof. In some embodiments, the second stent 765 may include one or more second anchoring regions (not shown) to promote tissue growth between the GI tract 732 and the second scaffold 768.

Figure 9A:
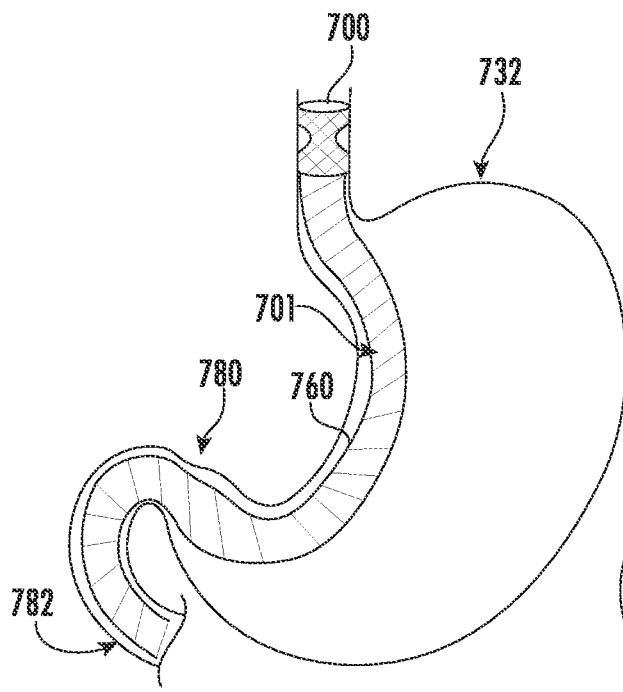
FIG. 9A demonstrates a system placed within a GI tract during a restrictive bariatric treatment according to embodiments of the present disclosure.
Figure 9B:
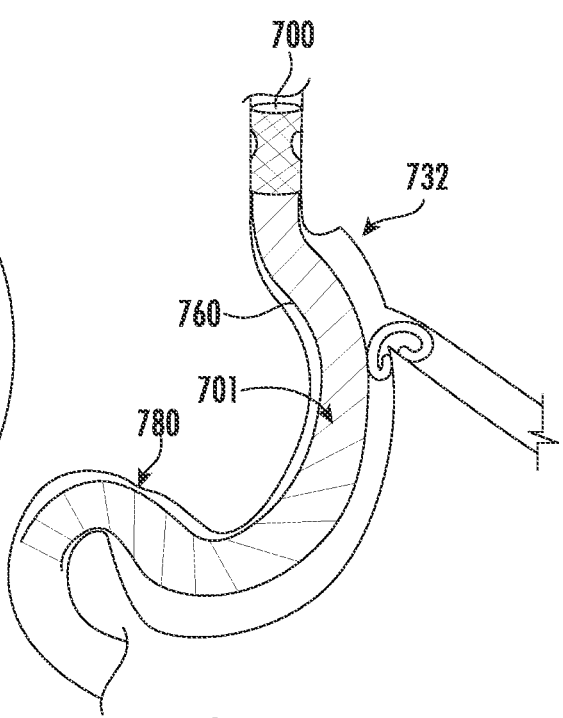
FIG. 9B demonstrates a system placed within a GI tract for treatment of leaks according to embodiments of the present disclosure.

In some embodiments, the system 701 may not include a second stent connected to the sheath 760. For example, as shown in FIGS. 9A-9B, the stent 700 may be positioned within a proximal section of the GI tract 732, while the sheath 760 may extend down further into the GI tract 732. In some embodiments, the sheath 760 may extend beyond the pyloric region 780 of the GI tract 732. Although non-limiting, FIG. 9A demonstrates the system 701 placed within the GI tract 732 for a restrictive bariatric treatment, while FIG. 9B demonstrates the system 701 used for the treatment of leaks, for example, intestinal fistula, extraintestinal fistula, gastrocutaneous fistula, complex fistula, etc. As shown in FIG. 9A, the sheath 760 may extend even further along the GI tract 732, for example, into a duodenum 782 (also known as gastrojejunal bypass (GJ bypass)).

Figure 10:
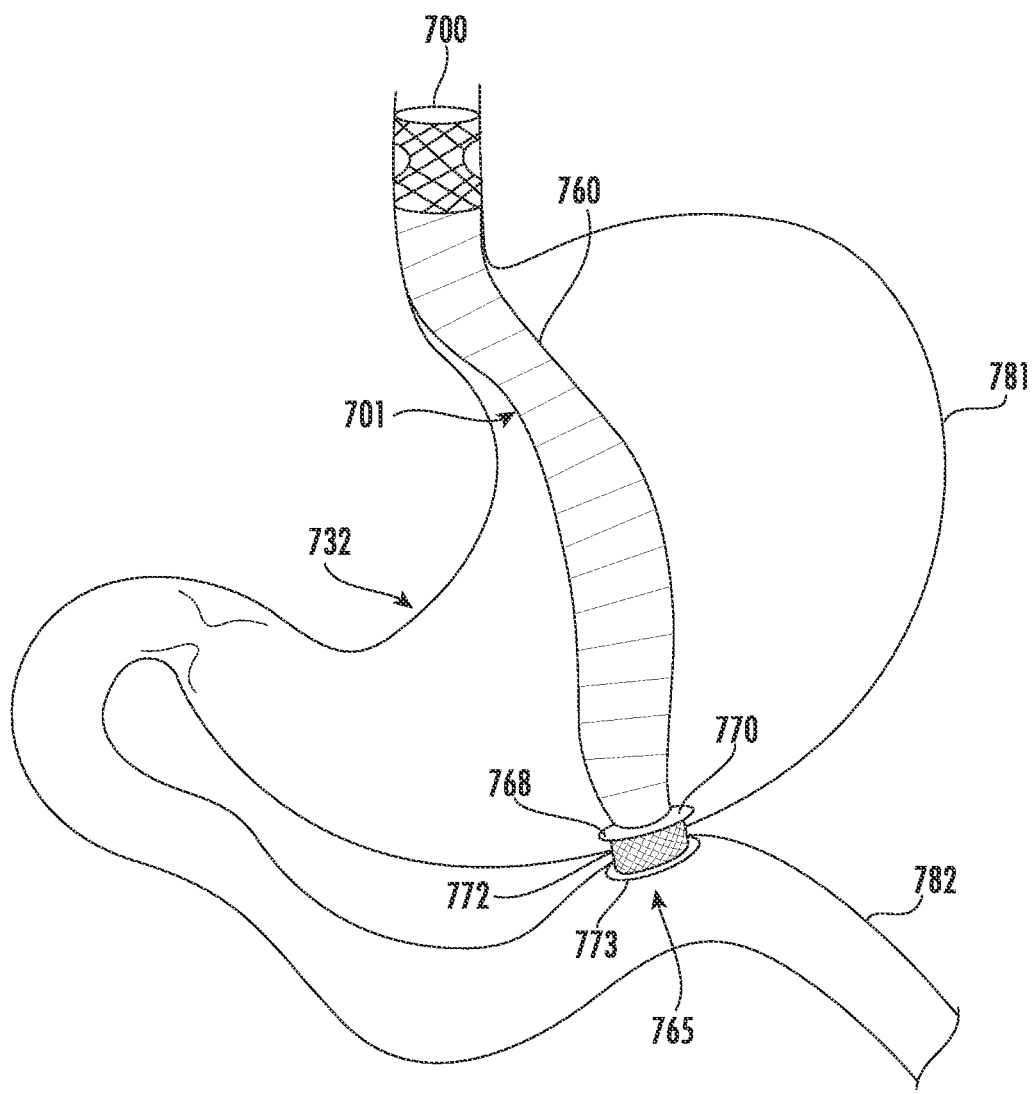
FIG. 10 demonstrates a system placed within a GI tract for treatment of leaks according to embodiments of the present disclosure.

Turning now to FIG. 10, the system 701 in use within a patient according to another embodiment of the present disclosure will be described. Although non-limiting, the system 701 may be particularly effective during a restrictive bariatric treatment using, for example, a gastro-jejunum bypass. As shown, the stent 700 may be positioned within a proximal section of the GI tract 732, while the sheath 760 may extend through a stomach 781 of the patient. The second stent 765, which is coupled to the sheath 760, may also be positioned within the GI tract 732, for example, between both the stomach 781 and a duodenum 782 extending from the stomach 781. As shown, the second scaffold 768 of the second stent 765 may be positioned such that the first flared section 770 is located within the stomach 781, while the second flared section 773 is located within the duodenum 782. The second medial section 772 may extend between the first flared section 770 and the second flared section 773, creating a bypass between the stomach 781 and the duodenum 782. Although not shown in FIG. 10, the second liner 775 may extend through the second medial section 772. Furthermore, one or more anchoring regions may be located along the first flared section 770, the second flared section 773, and/or the second medial section 772 to secure the second stent 765 in place between the stomach 781 and the duodenum 782.

Figure 11:
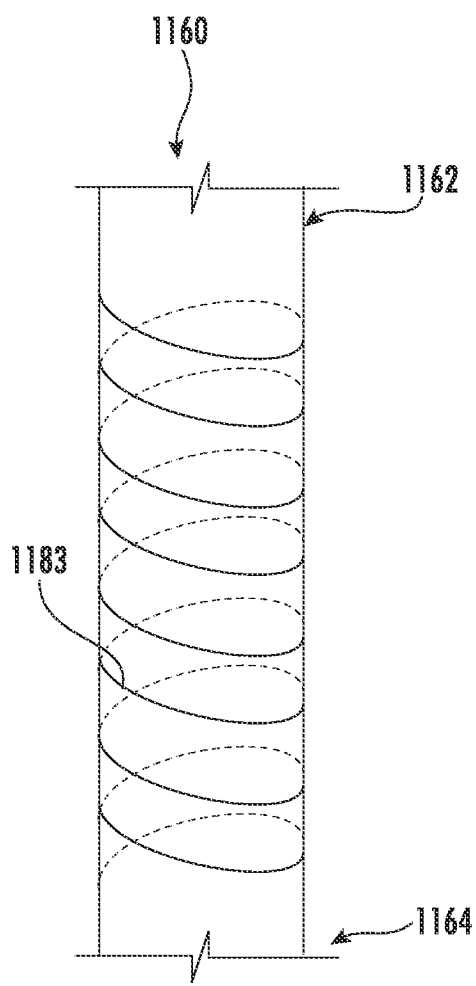
FIG. 11 is a side perspective view of a sheath according to embodiments of the present disclosure.

In FIG. 11, a sheath 1160 according to embodiments of the present disclosure is shown. The sheath 1160 may include a structural support element 1183 extending along a length of the sheath 1160, for example, between a proximal end 1162 and a distal end 1164. In some embodiments, the structural support element 1183 may be a spiral or helical rib extending along the sheath 1160. The structural support element 1183 may be disposed along an inner and/or outer surface of the sheath 1160, or may be embedded within the sheath 1160, for example, between one or more layers thereof. The structural support element 1183 may provide rigidity to the sheath 1160. In non-limiting embodiments, the structural support element 1183 may be made from enhanced, thickened or tubular hollow, tubular solid strips of the native polymer or denser polymer. Additionally, or alternatively, the structural support element may include sections of a more rigid material, e.g., nitinol, stainless steel, etc.

Figure 12:
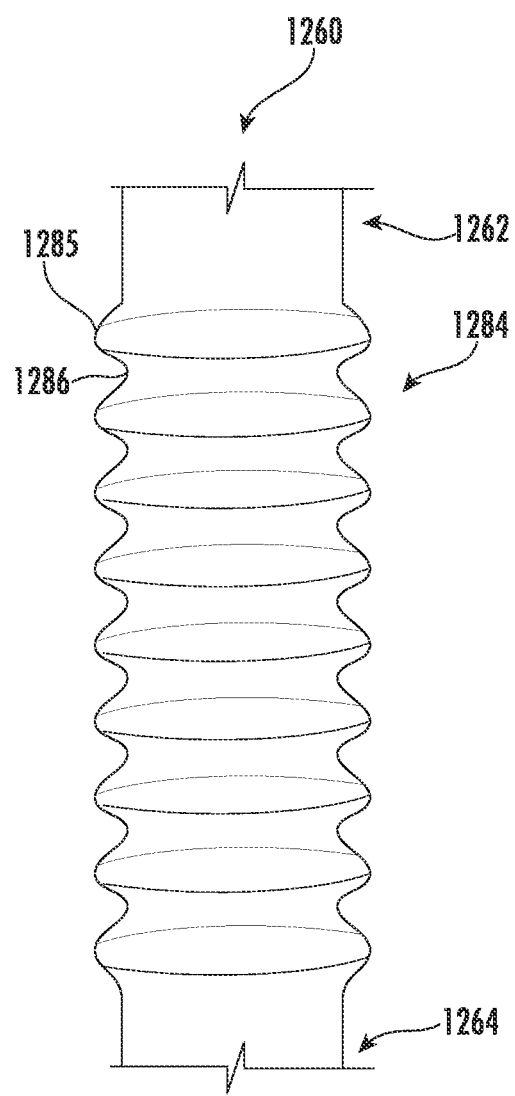
FIG. 12 is a side perspective view of a sheath according to embodiments of the present disclosure.

In FIG. 12, a sheath 1260 according embodiments of the present disclosure is shown. The sheath 1260 may include a flexible section 1284 disposed between a proximal end 1262 and a distal end 1264. In some embodiments, the flexible section 1284 includes a length of corrugated material arranged as a series of ridges 1285 and furrows 1286. The flexible section 1284 may provide flexibility to the sheath 1260. In some embodiments, the flexible section 1284 may include one or more structural support members. In non-limiting embodiments, the series of ridges 1285 and furrows 1286 of the corrugated material may correspond to a plurality of ripples formed in the sheath 1260. The series of ridges 1285 and furrows 1286 may also be formed by placing strips of alternating density or alternating thickness next to one another. Alternatively, or additionally, the series of ridges 1285 and furrows 1286 may be formed by placing strips of alternate polymer layers with differing elasticity strips adjacent to each other. Alternatively, or additionally, the series of ridges 1285 and furrows 1286 may be formed by an embedded rib(s) manufactured from materials such as Nitinol, stainless steel, etc.

Figure 13:
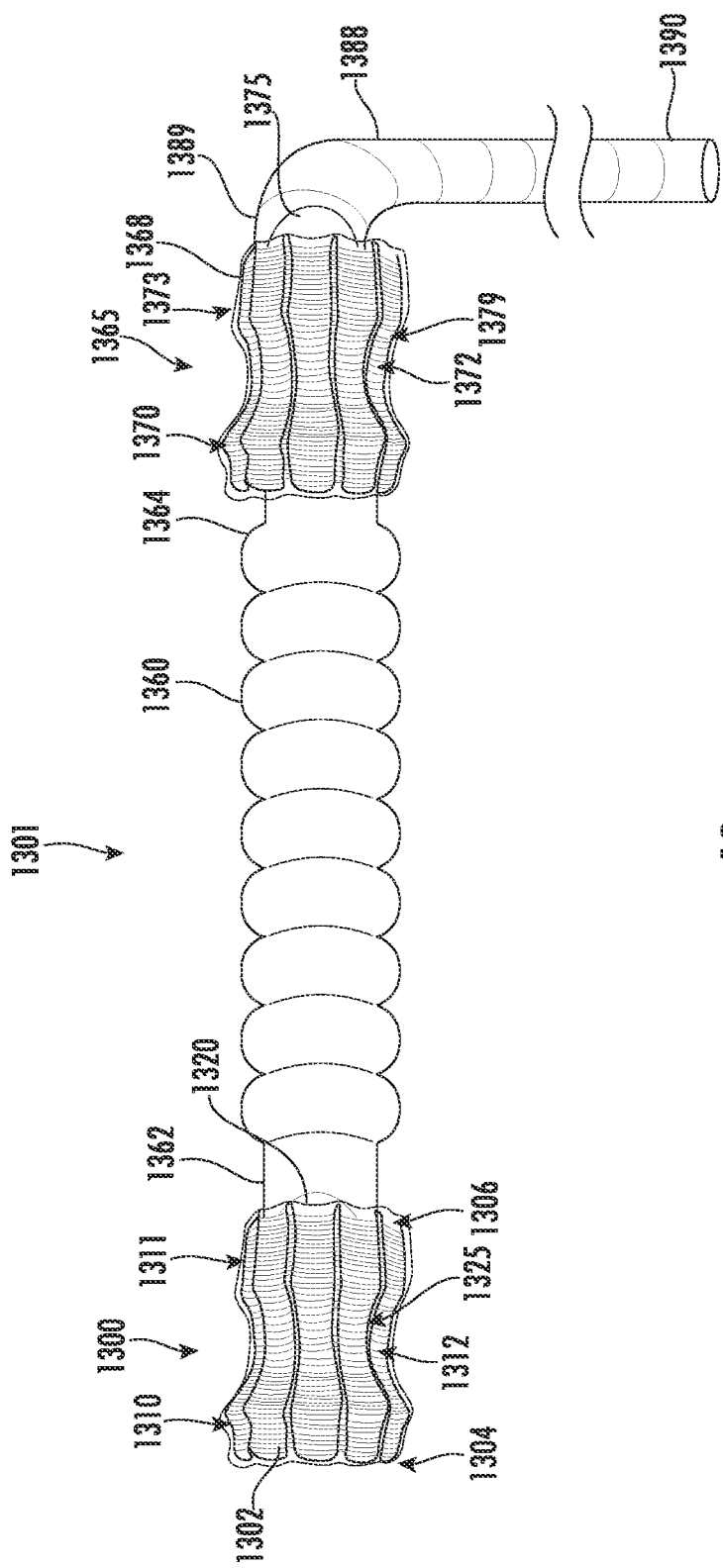
FIG. 13 is a side perspective view of a system according to embodiments of the present disclosure.

Turning now to FIG. 13, a system 1301 according to embodiments of the present disclosure will be described. The system 1301 may be the same or similar in many aspects to the system 701 described above. As such, only certain aspects of the system 1301 may be described hereinafter for the sake of brevity.

As shown, the system 1301 may include a first stent 1300 and a second stent 1365 coupled together by a first sheath 1360. For example, a first end 1362 of the first sheath 1360 may be coupled to the first stent 1300, while a second end 1364 of the first sheath 1360 may be coupled to the second stent 1365. In some embodiments, the first sheath 1360 may be a flexible conduit defining a lumen. Although non-limiting, the first sheath 1360 may include one or more structural support elements and/or flexible sections.

The system 1301 may further include a second sheath 1388 extending from the second stent 1365. The second sheath 1388 may include a proximal end 1389 coupled the second stent 1365, and a distal end 1390 extending farther within a GI tract of a patient. The second sheath 1388 may be the same or similar to the first sheath 1360. In other embodiments, the second sheath 1388 may be different than the first sheath 1360, for example, depending on a location of use within a GI tract of the patient. Although not shown, it will be appreciated that an additional stent may be connected to the second sheath 1388, for example, at the distal end 1390 thereof.

As shown, the first stent 1300 may include a first flared section 1310 at a first end 1304, and a second flared section 1311 at a second end 1306. Between the first flared section 1310 and the second flared section 1311 lies a medial section 1312. As shown, the medial section 1312 may have a reduced diameter as compared to the diameters of the first and second flared sections 1310, 1311. The first sheath 1360 may extend from, and connect with, the second end 1306 of the first stent 1300.

In some embodiments, the first stent 1300 may include a liner 1320 disposed along a surface of a scaffold 1302. The liner 1320 may be spaced from an anchoring region 1325 along the scaffold 1302 to promote tissue ingrowth with the GI tract. Although non-limiting, the anchoring region 1325 may be disposed along the first flared section 1310, the second flared section 1311, and/or the medial section 1322.

As further shown, the second stent 1365 may be the same or similar to the first stent 1300 in some embodiments. For example, a second scaffold 1368 of the second stent 1365 may include a first flared section 1370 and a second flared section 1373 connected by a second medial section 1372. In some embodiments, a second liner 1375 may extend along a surface (e.g., inner and/or outer) of the second scaffold 1368. The second liner 1375 may be spaced from the second scaffold 1368 in one or more second anchoring regions 1379 to promote tissue ingrowth between the second scaffold 1368 and the GI tract. Although non-limiting, the second anchoring regions 1379 may be disposed along the first flared section 1370, the second flared section 1373, and/or the second medial section 1372.

Figure 14A:
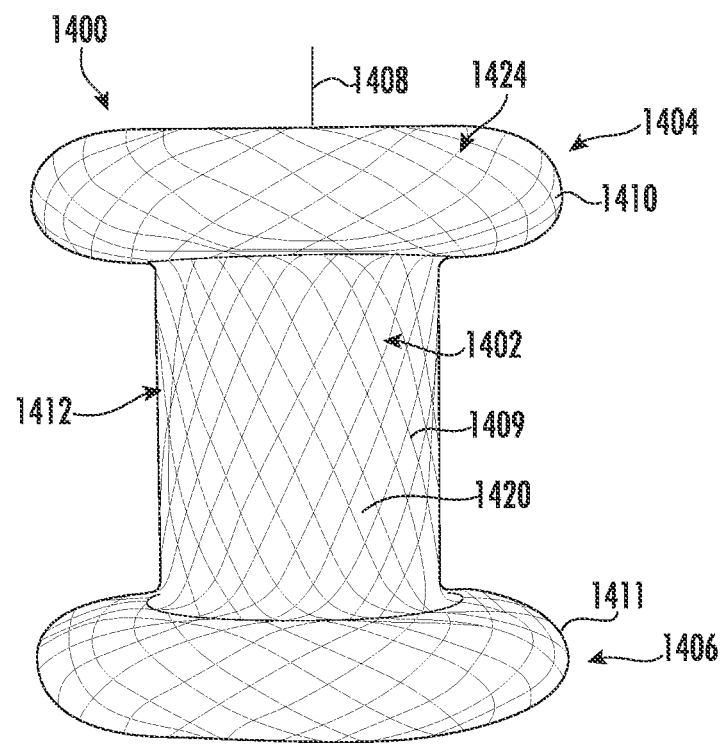
FIG. 14A is a side perspective view of a stent according to embodiments of the present disclosure.
Figures 14B, 14C:
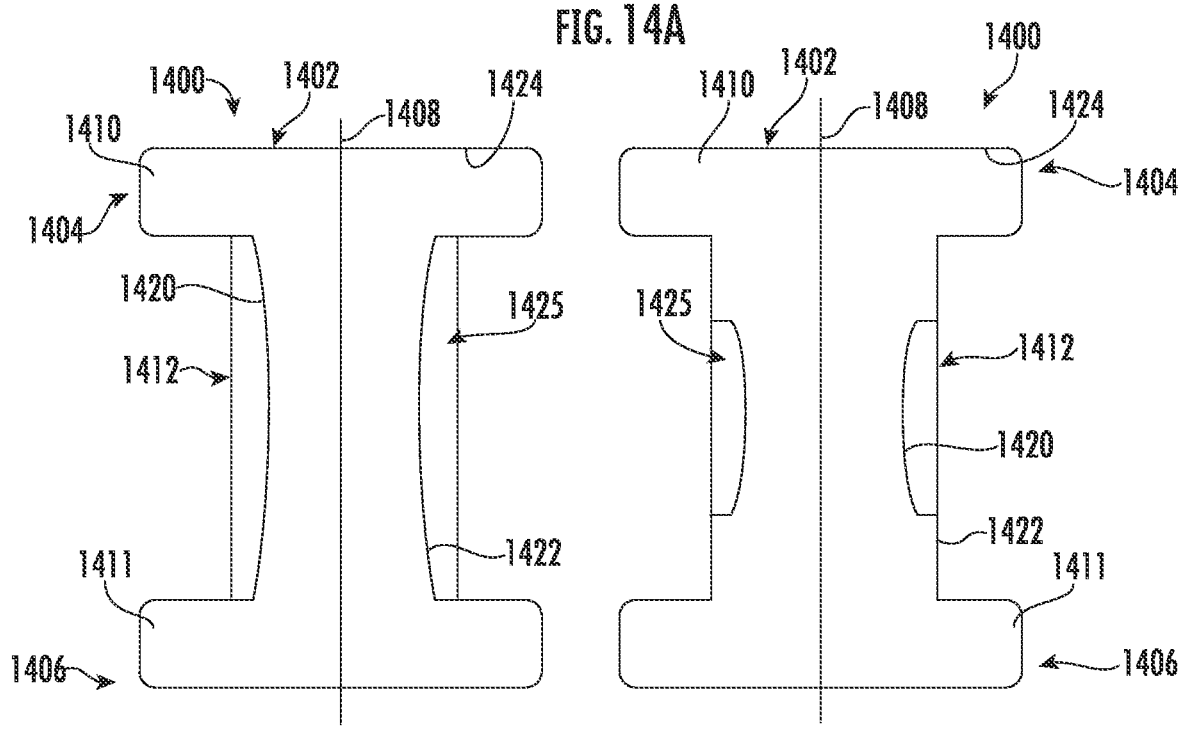
FIG. 14B is a side cross-sectional view of the stent of FIG. 14A according to an embodiment of the present disclosure.
FIG. 14C is a side cross-sectional view of the stent of FIG. 14A according to an embodiment of the present disclosure.

Turning now to FIGS. 14A-14C, a stent 1400 according to embodiments of the present disclosure will be described in greater detail. As shown, a scaffold 1402 of the stent 1400 may have a first end 1404 opposite a second end 1406, wherein the scaffold 1402 defines a lumen extending between the first end 1404 and second end 1406, for example, along a central longitudinal axis 1408.

The stent 1400 may include one or more strut members 1409 (FIG. 14A) forming the tubular scaffold 1402. The strut members 1409 may extend along the stent helically, longitudinally, circumferentially, or otherwise. As further shown, the scaffold 1402 may include a first flared/flanged section 1410 and a second flared/flanged section 1411 connected to, or integrally formed with, a medial section 1412. In some embodiments, a diameter of the first and/or second flared sections 1410, 1411 may be greater than a diameter of the medial section 1412. As shown, the medial section 1412 may generally have a uniform diameter along its length.

In some embodiments, the stent 1400 may be balloon or self-expanding. Self-expanding stent examples may include stents having one or more strut members 1409 combined to form a rigid and/or semi-rigid stent structure. For example, the strut members 1409 may be wires or filaments which are braided, wrapped, intertwined, interwoven, weaved, knitted, looped (e.g., bobbinet-style), or the like to form the stent structure. Alternatively, the stent 1400 may be a monolithic structure formed from a cylindrical tubular member, such as a single, cylindrical tubular laser-cut Nitinol tubular member, in which the remaining portions of the tubular member form the strut members 1409. Openings or interstices through the wall of the stent 1400 may be defined between adjacent strut members 1409.

The stent 1400 in examples disclosed herein may be constructed from a variety of materials. For example, when balloon or self-expandable, the stent 1400 may be constructed from a metal (e.g., Nitinol, Elgiloy, etc.). In other examples, the stent 1400 may be constructed from a polymeric material (e.g., PET). In yet other examples, the stent 1400 may be constructed from a combination of metallic and polymeric materials. In still yet other examples, the stent 1400 may include a bioabsorbable and/or biodegradable material.

As further shown, the stent 1400 may include a liner 1420 extending partially along the scaffold 1402. In the non-limiting embodiment shown, the liner 1420 may be formed along an interior surface 1424 of the scaffold 1402. In other embodiments, the liner 1420 may be formed along an exterior surface 1422 of the scaffold 1402. In yet other embodiments, the liner 1420 may be formed along both the exterior surface 1422 and the interior surface 1424 of the scaffold 1402.

Furthermore, the liner 1420 may include one or more layers joined together, wherein the liner 1420 is provided along the scaffold 1402 to prevent or minimize tissue ingrowth. In some embodiments, the liner 1420 may be an elastomeric or non-elastomeric material. As shown, the liner 1420 may extend between strut members 1409, thereby filling any space between adjacent strut members 1409 of the scaffold 1402.

In some embodiments, the liner 1420 is connected to the scaffold 1402 along the first flared/flanged section 1410 and the second flared/flanged section 1411, and spaced from an anchoring region 1425 of the medial section 1412 to promote tissue ingrowth between a GI tract and the scaffold 1402 of the medial section 1412. For example, the liner 1420 at the anchoring region 1425 may extend radially inward towards the central longitudinal axis 1408 such that the liner 1420 is generally not in contact with the interior surface 1424 of the scaffold 1402 along the medial section 1412. As shown in FIG. 14B, the anchoring region 1425 may generally extend along an entire length of the medial section 1412. As shown in FIG. 14C, the anchoring region 1425 may extend along only a portion of the medial section 1412. It will be appreciated that the size of the anchoring region 1425 may be selected to increase or decrease an amount of tissue ingrowth between the medial section 1412 and the GI tract. Embodiments herein are not limited in this context.

Figures 15A, 15B:
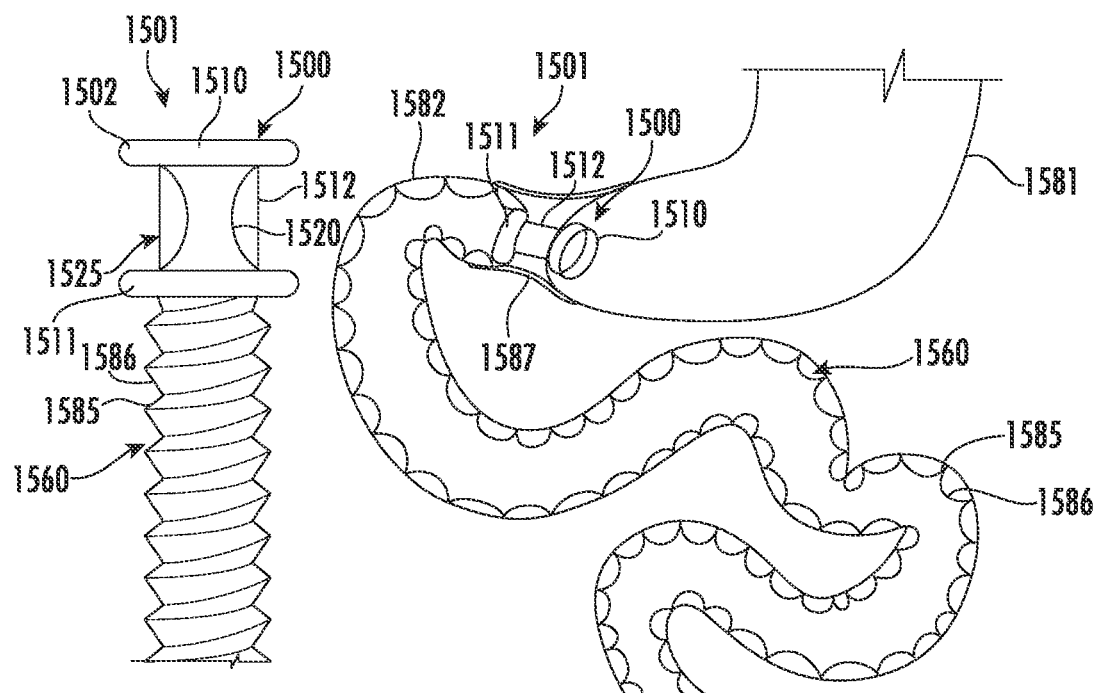
FIG. 15A is a side view of a system according to embodiments of the present disclosure.
FIG. 15B demonstrates the system of FIG. 15A within a GI tract according to embodiments of the present disclosure.

Turning now to FIGS. 15A-15B, a system 1501 according to embodiments of the present disclosure will be described. As shown, the system 1501 may include a stent 1500 coupled to a sheath 1560. The stent 1500 may be the same or substantially the same as the stent 1400 described above. As shown in FIG. 15B, the stent 1500 may be used to connect a stomach 1581 and a duodenum 1582 of a patient, with the sheath 1560 extending farther into the duodenum 1582. More specifically, a scaffold 1502 of the stent 1500 may be positioned such that a first flared section 1510 is located within the stomach 1581, while a second flared section 1511 is located within the duodenum 1582. A medial section 1512 may extend between the first flared section 1510 and the second flared section 1511, creating a bypass between the stomach 1581 and the duodenum 1582.

A liner 1520 (FIG. 15A) may extend through the medial section 1512. The liner 1520 may be spaced from an interior surface 1522 of the scaffold 1502 to create one or more anchoring regions 1525 along the medial section 1512. The anchoring regions 1525 may promote tissue growth to secure the stent 1500 in place between the stomach 1581 and the duodenum 1582, for example, across a pyloric valve 1587 as demonstrated in FIG. 15B.

In some embodiments, the sheath 1560 may be a length of corrugated material extending through the duodenum 1582. The corrugated material may be defined by a series of ridges 1585 and furrows 1586, wherein the corrugated material may provide flexibility to the sheath 1560 for traversing the duodenum 1582. In some embodiments, the corrugated material may also act as a liner to inhibit nutritional uptake, for example, to treat diabetes and and/or promote weight loss.

Figure 16:
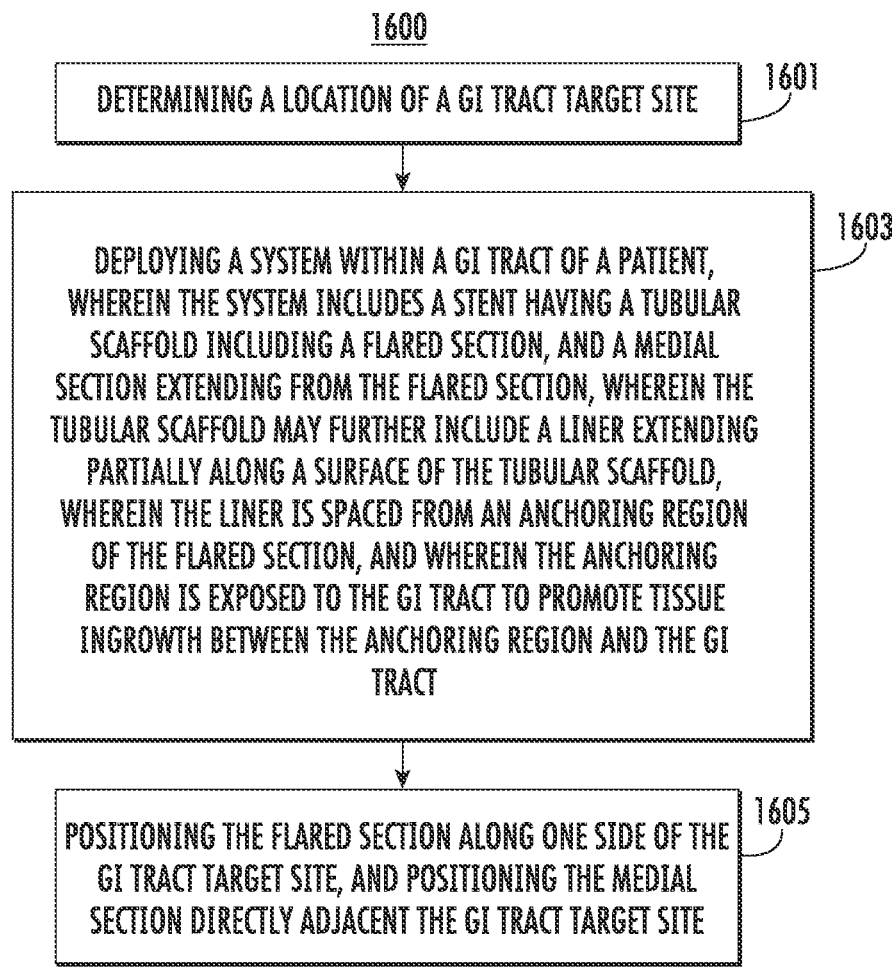
FIG. 16 is a flow diagram of a method according to embodiments of the present disclosure.

FIG. 16 is a flow diagram of a method 1600 according to embodiments of the present disclosure. At block 1601, the method 1600 may include determining a location of the GI tract target site, wherein the GI tract target site corresponds to a defect of the GI tract.

At block 1603, the method 1600 may include deploying a system within the GI tract of a patient, wherein the system includes a stent having a tubular scaffold including a flared section, and a medial section extending from the flared section, wherein the tubular scaffold may further include a liner extending partially along a surface of the tubular scaffold, wherein the liner is spaced from an anchoring region of the flared section, and wherein the anchoring region is exposed to the GI tract to promote tissue ingrowth between the anchoring region and the GI tract.

At block 1605, the method 1600 may include positioning the flared section along one side of a GI tract target site, and positioning the medial section directly adjacent the GI tract target site. In some embodiments, mucosal abrasion of the insertion site within the GI tract is used to promote tissue ingrowth between one or more regions or sections of the stent, such as the anchoring regions, and the GI tract, such as to mitigate migration of the stent from the target site. In some embodiments, the method 1600 may further include bypassing a portion of the GI tract using a sheath extending from the second end of the tubular scaffold, the sheath having a proximal end opposite a distal end, wherein a lumen extends between the proximal and distal ends. In some embodiments, the method 1600 may further include securing a second stent within the GI tract, the second stent coupled to the distal end of the sheath. In some embodiments, mucosal abrasion of the insertion site within the GI tract is used to promote tissue ingrowth between one or more regions or sections of the second stent, such as the anchoring regions, and the GI tract, such as to mitigate migration of the second stent from the target site.

The stents described herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the stents, and other components of the stents described herein, may also be doped with, made of, or otherwise include a radiopaque material. Radiopaque materials are understood to be materials capable of producing a relatively bright image on a fluoroscopy screen or another imaging technique during a medical procedure. This relatively bright image aids users in determining the stent's location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents to achieve the same result.

In some embodiments, a degree of Magnetic Resonance Imaging (MRI) compatibility is imparted into the stents described herein. For example, stents and other components of the stents, or portions thereof, may be made of a material that does not substantially distort the image and create substantial artifacts (e.g., gaps in the image). The stents may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 1600 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A stent, comprising:
   a tubular scaffold having a longitudinal extent with a first end opposite a second end and an anchoring region at an anchoring position along the longitudinal extent, and defining a lumen extending between the first end and the second end, the tubular scaffold comprising:
a flared section; and
a medial section extending longitudinally from the flared section;
wherein a diameter of the flared section is greater than a diameter of the medial section; and
a liner extending at least partially along the tubular scaffold;
wherein:
the anchoring region of the tubular scaffold has a shape distinct from the shape of a region of the tubular scaffold proximal to the anchoring region and proximal a region of the tubular scaffold distal to the anchoring region; and
a portion of the liner located along the longitudinal extent of the tubular scaffold at the same position as the anchoring position is spaced radially-inwardly from and within the anchoring region of the tubular scaffold to promote tissue ingrowth with the anchoring region of the tubular scaffold.

2. The stent of claim 1, wherein the anchoring region is a medial anchoring region along the medial section of the scaffold to promote tissue ingrowth with the medial section.

3. The stent of claim 2, wherein the medial anchoring region is provided at an expanded portion of the medial section, and wherein the expanded portion has a third diameter greater than the diameter of the medial section.

4. The stent of claim 3, wherein the liner is radially-inwardly spaced from and within the expanded portion to promote tissue ingrowth with the expanded portion.

5. The stent of claim 1, wherein the anchoring region is located along a sloped portion of the flared section, and wherein the sloped portion extends away from a central longitudinal axis extending through the lumen.

6. The stent of claim 1, wherein the medial section has a substantially uniform diameter.

7. The stent of claim 1, wherein the flared section has a first scaffold configuration, wherein the medial section has a second scaffold configuration, and wherein the first and second scaffold configurations are different.

8. A system, comprising:
a stent comprising:
a tubular scaffold having a longitudinal extent with a first end opposite a second end and an anchoring region along the longitudinal extent, and defining a lumen extending between the first end and the second end, the tubular scaffold comprising:
a flared section; and
a medial section extending longitudinally from the flared section;
wherein:
the anchoring region has a shape distinct from the shape of a region of the tubular scaffold proximal to the anchoring region and a region of the tubular scaffold distal to the anchoring region; and
a first diameter of the flared section is greater than a second diameter of the medial section; and
a liner extending at least partially along the tubular scaffold, wherein a portion of the liner located along the longitudinal extent of the tubular scaffold at the same position as the anchoring region of the tubular scaffold is spaced radially-inwardly from and within—the anchoring region to promote tissue ingrowth with the anchoring region and between the regions of the tubular scaffold proximal and distal to the anchoring region; and a sheath extending from the second end of the tubular scaffold, the sheath having a proximal end opposite a distal end, wherein a lumen extends between the proximal end and the distal end.

9. The system of claim 8, further comprising a second stent coupled to the distal end of the sheath.

10. The system of claim 9, the second stent comprising:
a second tubular scaffold; and
a second liner extending partially along a surface of the second tubular scaffold.

11. The system of claim 10, the second tubular scaffold comprising:
a second flared section; and
a second medial section extending from the second flared section, wherein a first diameter of the second flared section is greater than a second diameter of the second medial section, and wherein the second liner is spaced from and within a second anchoring region of the second flared section to promote tissue ingrowth with the second flared section.

12. The system of claim 8, wherein the anchoring region is a medial anchoring region along the medial section of the scaffold to promote tissue ingrowth with the medial section.

13. The stent of claim 8, wherein the anchoring region is located along a sloped portion of the flared section, and wherein the sloped portion extends away from a central longitudinal axis extending through the lumen.

14. The stent of claim 8, wherein the medial section includes an expanded portion, the expanded portion having a third diameter greater than the diameter of the medial section.

15. The stent of claim 14, wherein the liner is radially-inwardly spaced from and within the expanded portion to promote tissue ingrowth with the expanded portion.

16. The stent of claim 8, wherein the sheath comprises a structural support element.

17. A method, comprising:
deploying a system within a gastrointestinal (GI) tract of a patient, the system comprising:
a stent comprising:
a tubular scaffold having a longitudinal extent with a first end opposite a second end and an anchoring region at an anchoring position along the longitudinal extent, and defining a lumen extending between the first end and the second end, and wherein the tubular scaffold comprises:
a flared section;
a medial section extending longitudinally from the flared section;
wherein:
the anchoring region has a shape distinct from the shape of a region of the tubular scaffold proximal to the anchoring region and a region of the tubular scaffold distal to the anchoring region; and
a diameter of the flared section is greater than a diameter of the medial section; and
a liner extending at least partially along the tubular scaffold, wherein a portion of the liner located along the longitudinal extent of the tubular scaffold at the same position as the anchoring position is spaced radially-inwardly from and within the anchoring region of the tubular scaffold such that the anchoring region is exposed to the GI tract to promote tissue ingrowth between the anchoring region of the tubular scaffold and the GI tract; and positioning the tubular scaffold in the GI tract with the flared section along one side of a GI tract target site, and positioning the medial section directly adjacent the GI tract target site, with the anchoring region of the tubular scaffold adjacent tissue in the GI tract to promote tissue ingrowth therewith.

18. The method of claim 17, further comprising determining a location of the GI tract target site, wherein the GI tract target site corresponds to a leak of the GI tract.

19. The method of claim 17, further comprising bypassing a portion of the GI tract using a sheath extending from the second end of the tubular scaffold, the sheath having a proximal end opposite a distal end, wherein a lumen extends between the proximal and distal ends.

20. The method of claim 19, further comprising securing a second stent within the GI tract, the second stent coupled to the distal end of the sheath.

* * * * *